United States Patent
Gall et al.

(10) Patent No.: US 6,660,845 B1
(45) Date of Patent: Dec. 9, 2003

(54) NON-AGGREGATING, NON-QUENCHING OLIGOMERS COMPRISING NUCLEOTIDE ANALOGUES; METHODS OF SYNTHESIS AND USE THEREOF

(75) Inventors: Alexander A. Gall, Bothell, WA (US); Igor V. Kutyavin, Bothell, WA (US); Nicolaas M. J. Vermeulen, Woodinville, WA (US); Robert O. Dempcy, Kirkland, WA (US)

(73) Assignee: Epoch Biosciences, Inc., Bothell, WA (US)

( * ) Notice: Subject to any disclaimer, the term of this patent is extended or adjusted under 35 U.S.C. 154(b) by 0 days.

(21) Appl. No.: 09/447,936

(22) Filed: Nov. 23, 1999

(51) Int. Cl.[7] ............. C07H 21/00; C07H 21/02; C07H 21/04; C12Q 1/68
(52) U.S. Cl. ............. 536/23.1; 536/22.1; 536/24.3; 536/25.3; 435/6
(58) Field of Search ............. 435/6; 536/22.1, 536/23.1, 24.3, 25.3

(56) References Cited

U.S. PATENT DOCUMENTS

| | | | |
|---|---|---|---|
| 5,176,996 A | 1/1993 | Hogan et al. | 435/6 |
| 5,210,015 A | 5/1993 | Gelfand et al. | 435/6 |
| 5,419,966 A | 5/1995 | Reed et al. | 428/406 |
| 5,422,251 A | 6/1995 | Fresco | 435/91.1 |
| 5,480,980 A | 1/1996 | Seela | 536/23.1 |
| 5,492,806 A | 2/1996 | Drmanac et al. | 435/5 |
| 5,512,667 A | 4/1996 | Reed et al. | 536/24.31 |
| 5,525,464 A | 6/1996 | Drmanac et al. | 435/6 |
| 5,539,082 A | 7/1996 | Nielsen et al. | 530/300 |
| 5,556,752 A | 9/1996 | Lockhart et al. | 435/6 |
| 5,594,121 A | 1/1997 | Froehler et al. | 536/23.5 |
| 5,714,331 A | 2/1998 | Buchardt et al. | 435/6 |
| 5,736,336 A | 4/1998 | Buchardt et al. | 435/6 |
| 5,766,855 A | 6/1998 | Buchardt et al. | 435/6 |
| 5,773,571 A | 6/1998 | Nielsen et al. | 530/300 |
| 5,801,155 A | 9/1998 | Kutyavin et al. | 514/44 |
| 5,824,796 A | 10/1998 | Petrie et al. | 536/26.7 |
| 5,844,106 A | 12/1998 | Seela et al. | 536/22.1 |
| 6,156,501 A | 12/2000 | McGall et al. | |

FOREIGN PATENT DOCUMENTS

| | | |
|---|---|---|
| EP | 0 286 028 A2 | 10/1988 |
| WO | WO 90/14353 | 6/1992 |
| WO | WO 92/10588 | 6/1992 |
| WO | WO 96/17957 | 6/1992 |
| WO | WO 92/20702 | * 11/1992 |
| WO | WO 96/32496 A2 A3 | 10/1996 |
| WO | WO 98/49180 | 11/1998 |
| WO | WO 99/40226 | 8/1999 |
| WO | WO 99/51621 | 10/1999 |
| WO | WO 99/51775 | 10/1999 |

OTHER PUBLICATIONS

Diederichsen et al. European Journal of Organic Chemistry 1998, pp. 827–835.*

Wittung et al. "Direct observation of strand invasion by peptide nucleic acid (PNA) into double–stranded DNA" JACS 1996, 118, pp. 7049–7054.*

(List continued on next page.)

*Primary Examiner*—Jezia Riley
(74) *Attorney, Agent, or Firm*—Townsend and Townsend and Crew LLP

(57) ABSTRACT

The invention provides compositions and methods for improved hybridization analysis utilizing DNA, RNA, PNA and chimeric oligomers in which one or more purine bases are substituted by a pyrazolo[5,4-d]pyrimidine or by a 7-deazapurine purine analogue. Reduced self-aggregation and reduced fluorescence quenching are obtained when the oligomers are used in various methods involving hybridization. Methods of synthesis, as well as novel synthetic precursors, are also provided.

55 Claims, 1 Drawing Sheet

OTHER PUBLICATIONS

Koppitz et al. "Formation of Oligonucleotide–PNA–Chimeras by template– directed ligation" JACS 1998, 120, pp. 4563–4569.*

Ausubel et al. (1987 and annual updates). *Current Protocols in Molecular Biology.* John Wiley & Sons, Inc., pp. iii–xii (Table of Contents).

Belousov et al. (1998). "Triplex targeting of a native gene in permeabilized intact cells: Covalent modification of the gene for the chemokine receptor CCR5," *Nucl. Acids Res.* 26(5):1324–1328.

Bicket et al. (Sep. 6, 1994). "A high throughput fluorogenic substrate for stromelysin (MMP–3)," *Ann. NY Acad. Sci.* 732:351–355.

Demidov et al. (Mar. 1995). "Kinetics and mechanism of polyamide ("peptide") nucleic acid binding to duplex DNA," *Proc. Natl. Acad. Sci. USA* 92:2637–2641.

During et al. (Aug. 1999). "PNAs breach the blood–brain barrier," *Nature Biotechnol.* 17:753–754.

Eckstein (ed.). (1991). *Oligonucleotides and Analogues: A Practical Approach.* IRL Press: Oxford, pp. ix–xvii (Table of Contents).

Efimov et al. (1998). "Synthesis and evaluation of some properties of chimeric oligomers containing PNA and phosphono–PNA residues," *Nucl. Acids. Res.* 26(2):566–577.

Egholm. (Jun. 21–23, 1999). "PNA: A DNA mimic with unique properties," in *Cambridge Healthtech Institute's Seventh Annual Nucleic Acid–Based Technologies.* Wyndham Washington Hotel: Washington, D.C., pp. 1 and 10.

Gait (ed.). (1984). *Oligonucleotide Synthesis: A Practical Approach.* IRL Press: Oxford, pp. vii–xiii (Table of Contents).

Gangamani et al. (1997). "Spermine conjugated peptide nucleic acids (spPNA): UV and fluorescence studies of PNA–DNA hybrids with improved stability," *Biochem. Biophys. Res. Comm.* 240:778–782.

Greene et al. (1991). "Reactive charts," in *Protective Groups in Organic Synthesis.* Second edition, John Wiley and Sons, Inc: NY., pp. 441–452.

Seela, F. and M. Zulauf. Nucleoside s & Nucleotides 18 (11&12), 2697–2709 (1999). Incorporation of 2'–deoxysangivamycin in DNA duplexes: The conversion of a pyrrolo [2,3–d]pyrimidine nitrile to a carboxamide upon oligonucleotide deprotection.

Seela, F., M. Zulauf and G. Becher. XIII International Round Table, Nucleosides, Nucleotides and Their Biological Applications, Montpellier, France, Poster 279, Sep. 6–10, 1998. Duplex stability of pyrazolo[3,4–d]pyrimidines DNA with bulky 7–substituents of lipophilic side chains.

Seela, F., and M. Zulauf. J. Chem. Soc., Perkin Trans. 1, 479–488 (1999). Synthesis of oligonucleotides containing pyrazolo[3,4–d]–pyrimidines: The influence of 7–substituted 8–aza–7–deazaadenines on the duplex structure and stability.

Seela, F., G. Becher, H. Rosemeyer, H. Reuter, G. Kastner, I.A. Mikhailopulo. Helvetica Chimica Acta 82, 105–124 (1999). The *high–anti* conformation of 7–halogenated 8–aza–7–deaza–2'–deoxyguanosines: A study of the influence of modified bases on the sugar structure of nucleosides.

Ramzaeva, N., C. Mittelbach and F. Seela. Nucleosides & Nucleotides, 18 (6&7), 1439–1440 (1999). 7–Deaza–2'–deoxyguanosines functionalized with 7–(ω–aminoalk–1–ynyl) residues.

Seela, F., G. Becher and M. Zulauf. Nucleosides & Nucleotides, 18 (6&7), 1399–1400 (1999). 8–aza–7–deazapurine DNA: Synthesis and duplex stability of oligonucleotides containing 7–substituted bases.

Murchie, et al. (1991). "Retinoblastoma suspectibility genes contain 5'sequences with a high propensity to form guanine–tetrad structures," *Nucl. Acid Res.* 20 (1):49–53.

Lohse, et al. (1997) "Flourescein–Conjugated Lysine Monomers for Solid Phase Synthesis of Fluorescent Peptides and PNA Oligomers," *Am. Chem. Soc.*

Haugland (ed.). (1996). *Handbook of Fluorescent Probes and Research Chemicals.* Sixth edition, Molecular Probes, Inc.: Eugene, OR., pp. xii–ix (Table of Contents).

Hawthorne et al. (1997) "Evaluation of some fluorogenic substrates for continuous assay of aminopeptidase P," *Anal. Biochem.* 253:13–17.

Lampe. (1997). "Factors influencing the extent and selectivity of alkylation within triplexes by reactive G/A motif oligonucleotides," *Nucl. Acids Res.* 25(20):4123–4131.

Lee et al. (1993). "Allelic discrimination by nick–translation PCR with fluorogenic probes," *Nucl. Acids Res.* 21(16):3671–3766.

Lee et al. (Aug. 1999). "Seven–color, homogeneous detection of six PCR products," *Biotechniques* 27:342–349.

Li et al. (1999). "Design, synthiesis, and spectroscopic properties of peptide–bridged flourescence energy–transfer cassettes," *Bioconj. Chem.* 10:241–245.

Livak et al. (1995). "Oligonucleotides with fluorescent dyes at opposite ends provide a quenched probe system useful for detecting PCR product and nucleic acid hybridization," *PCR Meth. App.* 4:357–362.

Maniatis et al. (1982). *Molecular Cloning: A Laboratory Manual.* Cold Spring Harbor Laboratory Press, pp. v–x (Table of Contents).

Matayoshi et al. (Feb. 1990). "Novel flourogenic substrates for assaying retroviral proteases by resonance energy transfer," *Science* 247:954–958.

Murchie et al. (1994). "Tetraplex folding of telomere sequences and the inclusion of adenine bases," *EMBO J.* 13(4):993–1001.

Nielsen et al. (Dec. 1991). "Sequence–selective recognition of DNA by strand displacement with a thymine–substituted polyamide," *Science* 254:1497–1500.

Ogilvie et al. (Aug. 1988). "Total chemical synthesis of a 77–nucleotide–long RNA sequence having methionine–acceptance activity," *Proc. Natl. Acad. Sci. USA* 85:5764–5768.

Peyman et al. (1997). "PHONA–PNA co–oligomers: Nucleic acid mimetics with interesting properties," *Angew. Chem. Int. Ed. Engl.* 36(24):2809–2812.

Rothman et al. (1999). "A new generation of flourescent chemosensors demonstrate improved analyte detection sensitivity and photobleaching resistance," *Bioorg. Med. Chem. Lett.* 9:509–512.

Sambrook et al. (1989). *Molecular Cloning: A Laboratory Manual.* Second Edition, Cold Spring Harbor Laboratory Press, pp. xi–xxxviii (Table of Contents).

Seela et al. (1985). "Solid–phase synthesis of the self–complimentary hexamer d(c⁷GpCpc⁷GpCpc⁷GpC) via the O–3'–phosphoramidite of 7–deaza–2'–deoxyguanosine," *Nucl. Acids Res.* 13(3):911–926.

Seela et al. (1985). "Synthesis of the β–D–deoxyribofuranoside of 6–amino–1 Hpyrazolo[3,4–*d*]–pyrimidin–4(5*H*)–one–A new isoster of 2'–deoxyguanosine," *Heterocycles* 23:2521–2524.

Seela et al. (1986). "Palindromic oligonucleotides containing 7–deaza–2'–deoxyguanosine: Solid phase synthesis of d[(p)GG*AATTCC] octamers and recognition by the endodeoxyribonuclease EcoRI," *Nucl. Acids Res.* 14(5)2319–2332.

Seela et al. (1987). "Palindromic octa–and dodecanucleotides containing 2'–deoxytubercidin: Synthesis, hairpin formation, and recognition by the endodeoxyribonuclease EcoRI," *Biochem.* 26(8):2232–2238.

Seela et al. (1988). "131. 8–aza–7–deaza–2'–deoxyguanosine: Phosphoramidite synthesis and properties of octanucleotides," *Helv. Chim. Acta.* 71:1191–1198.

Seela et al. (1988). "193. 8–aza–7–deazaadenine N⁸–and N⁹–(β–D–2'–deoxyribofuranosides): Building blocks for automated DNA synthesis and properties of oligodeoxyribonucleotides," *Helv. Chim. Acta.* 71:1813–1823.

Seela et al. (1989). "Alternating d(G–C)₃ hexanucleotides containing 7–deaza–2'–deoxyguanosine or 8–aza–7–deaza–2'–deoxyguanosine in place of dG," *Nucl. Acids Res.* 17(3): 901–910.

Sproat et al. (1989). "Highly efficient chemical synthesis of 2'–O–methyloligoribonucleotides and tetrabiotinylated derivatives; novel probes that are resistant to degradation by RNA or DNA specific nucleases," *Nucl. Acids Res.* 17(9):3373–3386.

Tominaga et al. (Mar./Apr. 1990). "Synthesis of pyrazolo[3, 4–d]pyrimidine derivatives using ketene dithioacetals," *J. Heterocycl. Chem.* 27:775–783.

Uhlmann et al. (1998). "PNA: Synthetic polyamide nucleic acids with unususal binding properties," *Angew. Chem. Int. Ed.* 37:2796–2823.

Uhlmann. (Jun. 21–23, 1999). "PNA/DNA chimeras: Properties and potential applications in therapy and diagnostics," in *Cambrige Healthtech Institute's Seventh Annual Nucleic Acid–Based Technologies*. Wyndham Washington Hotel: Washington, D.C.,.

Will et al. (1995). "The synthesis of polyamide nucleic acids using a novel monomethoxytrityl protecting–group strategy," *Tetrahedron* 51(44):12069–12082.

Wittwer et al. (Jan. 1997). "Continuous flourescence monitoring of rapid cycle DNA amplification," *Biotechniques* 22:130–138.

Wittwer et al. (Jan. 1997). "The lightcycler™: A microvolume mutisample fluorimeter with rapid temperature control," *Biotechniques* 22:176–181.

\* cited by examiner

SEQUENCE LISTING

<160> NUMBER OF SEQ ID NOS: 23

<210> SEQ ID NO 1
<211> LENGTH: 14
<212> TYPE: DNA
<213> ORGANISM: Artificial Sequence
<220> FEATURE:
<223> OTHER INFORMATION: synthetic construct

<400> SEQUENCE: 1
caaatggggg gggg   14

<210> SEQ ID NO 2
<211> LENGTH: 14
<212> TYPE: DNA

```
<213> ORGANISM: Artificial Sequence
<220> FEATURE:
<223> OTHER INFORMATION: synthetic construct

<400> SEQUENCE: 2
acaaatgggg gggg                                                        14

<210> SEQ ID NO 3
<211> LENGTH: 14
<212> TYPE: DNA
<213> ORGANISM: Artificial Sequence
<220> FEATURE:
<223> OTHER INFORMATION: synthetic construct

<400> SEQUENCE: 3
aacaaatggg gggg                                                        14

<210> SEQ ID NO 4
<211> LENGTH: 14
<212> TYPE: DNA
<213> ORGANISM: Artificial Sequence
<220> FEATURE:
<223> OTHER INFORMATION: synthetic construct

<400> SEQUENCE: 4
caacaaatgg gggg                                                        14

<210> SEQ ID NO 5
<211> LENGTH: 14
<212> TYPE: DNA
<213> ORGANISM: Artificial Sequence
<220> FEATURE:
<223> OTHER INFORMATION: synthetic construct

<400> SEQUENCE: 5
acaacaaatg gggg                                                        14

<210> SEQ ID NO 6
<211> LENGTH: 14
<212> TYPE: DNA
<213> ORGANISM: Artificial Sequence
<220> FEATURE:
<223> OTHER INFORMATION: synthetic construct

<400> SEQUENCE: 6
cacaacaaat gggg                                                        14

<210> SEQ ID NO 7
<211> LENGTH: 13
<212> TYPE: DNA
<213> ORGANISM: Artificial Sequence
<220> FEATURE:
<223> OTHER INFORMATION: synthetic construct

<400> SEQUENCE: 7
cacaacaaat ggg                                                         13

<210> SEQ ID NO 8
<211> LENGTH: 14
<212> TYPE: DNA
<213> ORGANISM: Artificial Sequence
<220> FEATURE:
<223> OTHER INFORMATION: synthetic construct

<400> SEQUENCE: 8
agcacaacaa atgg                                                        14
```

```
<210> SEQ ID NO 9
<211> LENGTH: 14
<212> TYPE: DNA
<213> ORGANISM: Artificial Sequence
<220> FEATURE:
<221> NAME/KEY: modified_base
<222> LOCATION: (6)...(14)
<223> OTHER INFORMATION: n = PPG
<223> OTHER INFORMATION: synthetic construct

<400> SEQUENCE: 9 caaatnnnn nnnn                                                      14

<210> SEQ ID NO 10
<211> LENGTH: 14
<212> TYPE: DNA
<213> ORGANISM: Artificial Sequence
<220> FEATURE:
<221> NAME/KEY: modified_base
<222> LOCATION: (7)...(14)
<223> OTHER INFORMATION: n = PPG
<223> OTHER INFORMATION: synthetic construct

<400> SEQUENCE: 10
acaaatnnnn nnnn                                                     14

<210> SEQ ID NO 11
<211> LENGTH: 14
<212> TYPE: DNA
<213> ORGANISM: Artificial Sequence
<220> FEATURE:
<221> NAME/KEY: modified_base
<222> LOCATION: (8)...(14)
<223> OTHER INFORMATION: n = PPG
<223> OTHER INFORMATION: synthetic construct

<400> SEQUENCE: 11
aacaaatnnn nnnn                                                     14

<210> SEQ ID NO 12
<211> LENGTH: 14
<212> TYPE: DNA
<213> ORGANISM: Artificial Sequence
<220> FEATURE:
<221> NAME/KEY: modified_base
<222> LOCATION: (9)...(14)
<223> OTHER INFORMATION: n = PPG
<223> OTHER INFORMATION: synthetic construct

<400> SEQUENCE: 12
caacaaatnn nnnn                                                     14

<210> SEQ ID NO 13
<211> LENGTH: 14
<212> TYPE: DNA
<213> ORGANISM: Artificial Sequence
<220> FEATURE:
<221> NAME/KEY: modified_base
<222> LOCATION: (10)...(14)
<223> OTHER INFORMATION: n = PPG
<223> OTHER INFORMATION: synthetic construct

<400> SEQUENCE: 13
acaacaaatn nnnn                                                     14

<210> SEQ ID NO 14
<211> LENGTH: 14
<212> TYPE: DNA
<213> ORGANISM: Artificial Sequence
```

```
<220> FEATURE:
<221> NAME/KEY: modified_base
<222> LOCATION: (11)...(14)
<223> OTHER INFORMATION: n = PPG
<223> OTHER INFORMATION: synthetic construct

<400> SEQUENCE: 14
cacaacaaat nnnn                                                              14

<210> SEQ ID NO 15
<211> LENGTH: 13
<212> TYPE: DNA
<213> ORGANISM: Artificial Sequence
<220> FEATURE:
<221> NAME/KEY: modified_base
<222> LOCATION: (11)...(13)
<223> OTHER INFORMATION: n = PPG
<223> OTHER INFORMATION: synthetic construct

<400> SEQUENCE: 15
cacaacaaat nnn                                                               13

<210> SEQ ID NO 16
<211> LENGTH: 14
<212> TYPE: DNA
<213> ORGANISM: Artificial Sequence
<220> FEATURE:
<221> NAME/KEY: modified_base
<222> LOCATION: (13)...(14)
<223> OTHER INFORMATION: n = PPG
<223> OTHER INFORMATION: synthetic construct

<400> SEQUENCE: 16
agcacaacaa atnn                                                              14

<210> SEQ ID NO 17
<211> LENGTH: 76
<212> TYPE: DNA
<213> ORGANISM: Artificial Sequence
<220> FEATURE:
<223> OTHER INFORMATION: synthetic construct

<400> SEQUENCE: 17
cacctcagcc tcccaagtaa cttttaaccc cccccatttt gttgtgctgt tttcatacct            60
gtaatcctgg cacttt                                                            76

<210> SEQ ID NO 18
<211> LENGTH: 13
<212> TYPE: DNA
<213> ORGANISM: Artificial Sequence
<220> FEATURE:
<223> OTHER INFORMATION: synthetic construct

<400> SEQUENCE: 18
gtcctgattt tac                                                               13

<210> SEQ ID NO 19
<211> LENGTH: 13
<212> TYPE: DNA
<213> ORGANISM: Artificial Sequence
<220> FEATURE:
<221> NAME/KEY: modified_base
<222> LOCATION: (1)...(1)
<223> OTHER INFORMATION: n = PPG
<223> OTHER INFORMATION: synthetic construct
```

<400> SEQUENCE: 19
ntcctgattt tac                                                      13

<210> SEQ ID NO 20
<211> LENGTH: 13
<212> TYPE: DNA
<213> ORGANISM: Artificial Sequence
<220> FEATURE:
<223> OTHER INFORMATION: synthetic construct

<400> SEQUENCE: 20
gtcctgattt tac                                                      13

<210> SEQ ID NO 21
<211> LENGTH: 13
<212> TYPE: DNA
<213> ORGANISM: Artificial Sequence
<220> FEATURE:
<221> NAME/KEY: modified_base
<222> LOCATION: (1)...(1)
<223> OTHER INFORMATION: n = PPG
<223> OTHER INFORMATION: synthetic construct

<400> SEQUENCE: 21
ntcctgattt tac                                                      13

<210> SEQ ID NO 22
<211> LENGTH: 16
<212> TYPE: DNA
<213> ORGANISM: Artificial Sequence
<220> FEATURE:
<223> OTHER INFORMATION: synthetic construct

<400> SEQUENCE: 22
acctgtattc cttgcc                                                   16

<210> SEQ ID NO 23
<211> LENGTH: 15
<212> TYPE: DNA
<213> ORGANISM: Artificial Sequence
<220> FEATURE:
<223> OTHER INFORMATION: synthetic construct
<220> FEATURE:
<221> NAME/KEY: modified_base
<222> LOCATION: (1)...(1)
<223> OTHER INFORMATION: n = PPG
<220> FEATURE:
<221> NAME/KEY: modified_base
<222> LOCATION: (6)...(6)
<223> OTHER INFORMATION: n = PPG
<220> FEATURE:
<221> NAME/KEY: modified_base
<222> LOCATION: (12)...(13)
<223> OTHER INFORMATION: n = PPG

<400> SEQUENCE: 23
ntacancaaa tnnaa                                                    15

NON-AGGREGATING, NON-QUENCHING OLIGOMERS COMPRISING NUCLEOTIDE ANALOGUES; METHODS OF SYNTHESIS AND USE THEREOF

TECHNICAL FIELD

The disclosure concerns the use of nucleotide analogues to provide improved properties to hybridization probes, including DNA and RNA probes and modified nucleic acid probes, such as peptide nucleic acids (PNAs), and to chimeric probes containing two or more types of nucleic acid and/or modified nucleic acid.

BACKGROUND

Hybridization analysis is central to a variety of techniques in molecular biology and diagnostics, including gene cloning, gene identification, forensic analysis, pharmacogenomics and identification of genetic polymorphisms. Hybridization can be used as an endpoint of an assay, whereby the presence of hybridized probe constitutes the readout for the assay; or hybridization can be used as an initial step in an assay, wherein an event subsequent to hybridization (such as, for example, extension of a hybridized primer or hydrolysis of a hybridized probe) is used as the readout.

Traditionally, hybridization probes and primers have been DNA molecules; however, there are certain disadvantages to the use of DNA as a probe or primer. For example, the base composition of a DNA molecule can affect its effectiveness as a probe or primer in several ways. A DNA molecule with a high concentration of G residues is often difficult to handle (e.g., problems with aggregation and poor solubility) and can yield high background in hybridization reactions. It is also well-known that G-rich DNA molecules are prone to the production of artifacts in the analysis of DNA sequences by gel electrophoresis, presumably due to the adoption of secondary structure by such molecules, despite the denaturing conditions under which such analyses are conducted.

Various modified forms of DNA and DNA analogues have been used in attempts to overcome some of the disadvantages of the use of DNA molecules as probes and primers. Among these are peptide nucleic acids (PNAs, also known as polyamide nucleic acids). Nielsen et al. (1991) *Science* 254:1497–1500. PNAs contain heterocyclic base units, as found in DNA and RNA, that are linked by a polyamide backbone, instead of the sugar-phosphate backbone characteristic of DNA and RNA. PNAs are capable of hybridization to complementary DNA and RNA target sequences and, in fact, hybridize more strongly than a corresponding nucleic acid probe. Furthermore, PNAs are resistant to many types of nuclease which attack the sugar-phosphate DNA and RNA backbones. Additional advantages of PNAs include the ability of specifically modified PNAs to cross the blood-brain-barrier and the observation that PNAs injected intrathecally can mediate antisense affects in vivo. During et al. (1999) *Nature Biotechnol.* 17:753–754.

The synthesis of PNA oligomers and reactive monomers used in the synthesis of PNA oligomers have been described in U.S. Pat. Nos. 5,539,082; 5,714,331; 5,773,571; 5,736,336 and 5,766,855. Alternate approaches to PNA synthesis and monomers for PNA synthesis have been summarized. Uhlmann et al. (1998) *Angew. Chem. Int. Ed.* 37:2796–2823.

However, as they become more widely used, disadvantages of PNAs are also becoming apparent. For example, long PNA oligomers, depending on their sequence, are prone to aggregation, difficult to purify and difficult to characterize. In addition, purine-rich PNA oligomers tend to aggregate and are poorly soluble in aqueous media. Gangamani et al. (1997) *Biochem. Biophys. Res. Comm.* 240:778–782; Egholm, Cambridge Healthtech Institute's Seventh Annual Nucleic Acid-Based Technologies, Jun. 21–23, 1999, Washington, D.C.; Uhlmann, Cambridge Healthtech Institute's Seventh Annual Nucleic Acid-Based Technologies, Jun. 21–23, 1999, Washington, D.C. Consequently, effective use of PNAs in hybridization is limited to sequences in which there are no more than 4–5 consecutive purines, no more than 6 purines in any 10-base portion of the sequence, and/or no more than 3 consecutive G residues. See, for example, http://www.resgen.com/perseptivedesign.html. Furthermore, since PNA-PNA interactions are even stronger than PNA-DNA interactions, PNA-containing probes and primers containing self-complementary sequences cannot generally be used for hybridization to a target sequence. Another consequence of the very strong interaction between PNAs and complementary DNA and/or RNA molecules is that it is difficult to obtain single nucleotide mismatch discrimination using PNA probes. Demidov et al. (1995) *Proc. Natl. Acad. Sci. USA* 92:2637–2641.

Uhlmann et al., supra reviewed approaches for increasing the solubility of PNAs, including synthesis of PNA/DNA chimeras and addition of terminal lysine residues to a PNA oligomer. They did not disclose the use of nucleotide analogues to increase solubility and improve hybridization properties of PNA oligomers.

Similar design constraints are required in the synthesis of non-PNA-containing oligonucleotide probes and primers. See, for example, the publication entitled "Sequence Detection Systems Quantitative Assay Design and Optimization," PE Biosystems, Stock No. 117MI02-01. In these cases, the G/C content of an oligomer must be kept within the range of 20–80% and runs of an identical nucleotide, particularly guanine (G), should be avoided. In particular, the aforementioned publication advises against stretches of four or more G residues and against the presence of a G residue at the 5' end of a 5'-fluorescently labeled probe. In the case of primers, the five nucleotides at the 3' end should comprise no more than two G and/or C residues.

The synthesis of pyrazolo[3,4-d]pyrimidine and 7-deazapurine nucleosides, as well as their phosphoramidite monomers for use in oligomer synthesis, have been described. Seela et al (1985) *Nucl. Acids Res.* 13:911–926; Seela et al. (1988a) *Helv. Chim. Acta* 71:1191–1198; Seela et al. (1988b) *Helv. Chim. Acta* 71:1813–1823; and Seela et al. (1987) *Biochem.* 26:2232–2238. Pyrazolo[3,4-d] pyrimidine and 7-deazapurine nucleosides for use in DNA sequencing and as antiviral agents are disclosed in EP 286 028. Co-owned PCT publication WO 99/51775 discloses the use of pyrazolo[3,4-d]pyrimidine containing oligonucleotides for hybridization and mismatch discrimination. It has been reported that incorporation of 2'-deoxy-7-deazaguanosine into DNA eliminates band compression in GC-rich stretches during DNA sequence analysis by gel electrophoresis (U.S. Pat. No. 5,844,106), decreases tetraplex formation by G-rich sequences (Murchie et al. (1994) *EMBO J.* 13:993–1001) and reduces formation of aggregates characteristic of DNA molecules containing 2'-deoxyguanosine (U.S. Pat. No. 5,480,980). However, substitution of oligonucleotides with either 7-deazaadenosine (in place of A) or 7-deazaguanosine (in place of G) lowers the $T_m$ of hybrids formed by such substituted oligonucleotides, with greater than one degree reduction in $T_m$ per substituted base. Seela et al. (1987)

supra; and Seela et al. (1986) *Nucl. Acids Res.* 14:2319–2332.

On the other hand, stabilization of duplexes by pyrazolopyrimidine base analogues has been reported. Seela et al. (1988) *Helv. Chim. Acta.* 71:1191–1198; Seela et al. (1988) *Helv. Chim. Acta.* 71:1813–1823; and Seela et al. (1989) *Nucleic Acids Res.* 17:901–910. Oligonucleotides in which one or more purine residues have been substituted by pyrazolo[3,4-d]pyrimidines display enhanced duplex- and triplex-forming ability, as disclosed, for example, in Belousov et al. (1998) *Nucleic Acids Res.* 26:1324–1328; U.S. Pat. No. 5,594,121 and co-owned PCT publication WO 98/49180. Pyrazolo[3,4-d]pyrimidine residues in oligonucleotides are also useful as sites for attachment of various pendant groups to oligonucleotides. See co-owned PCT Publication WO 90/14353, Nov. 29, 1990 and U.S. Pat. No. 5,824,796. None of these references disclose the use of pyrazolopyrimidines or any other type of base analogue for reducing aggregation and/or increasing solubility of an oligomer, or for decreasing quenching of a fluorophore conjugated to an oligomer.

Conjugates comprising a minor groove binder (MGB), an oligonucleotide wherein one or more purine residues are substituted by a pyrazolo[3,4-d]pyrimidine (PZP) residue, a fluorophore and a fluorescence quencher have been disclosed in co-owned PCT publications WO 99/51621 and WO 99/51775. Such conjugates are used, among other things, as hybridization probes, primers and hydrolyzable probes in 5'-nuclease-based amplification assays. Inclusion of a MGB in these conjugates increases the stability of hybrids formed by the oligonucleotide portion of the conjugate, allowing the design of shorter probes. In addition, both the MGB and the PZP contribute to the ability of such conjugates to exhibit enhanced mismatch discrimination. Neither of the aforementioned publications disclose the use of PZPs or any other type of base analogue for reducing aggregation and/or increasing solubility of an oligomer, or for decreasing quenching of a fluorophore conjugated to an oligomer.

SUMMARY

Oligomers wherein at least one of the subunits comprises a pyrazolopyrimidine and/or a pyrrolopyrimidine base analogue are provided. The oligomers can comprise DNA, RNA, PNA, or any combination or chimera thereof. Any number of purine residues in the oligomer can be substituted by a base analogue. Any of the above-mentioned oligomers can comprise additional moieties such as fluorophores, fluorescence quenchers and/or minor groove binders.

Oligomers wherein at least one of the subunits comprises a pyrazolopyrimidine and/or a pyrrolopyrimidine base analogue, when used for hybridization, are less prone to aggregation and self-association, are more soluble, are capable of enhanced mismatch discrimination, and do not quench the emission of conjugated fluorescent labels.

Oligomers comprising one or more PNA residues wherein at least one of the PNA residues comprises a pyrazolopyrimidine and/or a pyrrolopyrimidine base analogue are also provided. The oligomers can comprise exclusively PNA residues, or the oligomers can comprise both PNA and/or DNA and/or RNA nucleotide residues to constitute a PNA/DNA, PNA/RNA or PNA/DNA/RNA chimera. Any number of purine residues in the oligomer can be substituted by a base analogue. Any of the above-mentioned oligomers can comprise additional moieties such as fluorophores, fluorescence quenchers and/or minor groove binders.

In another embodiment, compositions comprising a polymer and a fluorophore are provided, wherein one or more purine-containing residues of the polymer are substituted with a residue comprising a pyrazolopyrimidine and/or pyrrolopyrimidine base analogue. Polymers can comprise PNA, DNA, RNA or any combination or chimera thereof, and the base analogue can be present in any of the PNA, DNA or RNA portions of a chimeric polymer. Any number of purine residues in the polymer can be substituted by a base analogue, in any of the PNA, DNA and/or RNA portions. The above-mentioned compositions can optionally comprise a fluorescence quencher and/or a minor groove binder.

In the polymer-fluorophore compositions just described, quenching of the fluorophore by purine residues in the polymer is reduced when one or more purines are substituted with a base analogue. Such compositions additionally comprising a fluorescence quencher are useful, for example, as probes in hydrolyzable probe assays, in which quenching of the fluorophore by the fluorescence quencher is relieved by hybridization-dependent hydrolysis of probe. The reduction in quenching afforded by substitution of a base analogue for a purine leads to higher fluorescence output after hydrolysis and, hence, greater sensitivity in such assays.

New intermediates for the synthesis of PNA-containing oligomers comprising base analogues are also provided. In one embodiment, acetic acid derivatives of pyrazolopyrimidine and pyrrolopyrimidine base analogues, wherein $N^1$ of the pyrazolopyrimidine or pyrrolopyrimidine is linked to C2 of an acetic acid moiety and functional groups are blocked, are provided. These derivatives are useful for preparation of monomers for automated synthesis of substituted PNAs and PNA/DNA chimeras. Preferred embodiments of these intermediates include 2-{6-[(1E)-1-aza-2-(dimethylamino) vinyl]-4-hydroxypyrazolo[5,4-d]pyrimidinyl}acetic acid; 2-(6-amino-4-hydroxypyrazolo[5,4-d]pyrimidinyl)acetic acid; and 2-(-4-aminopyrazolo[5,4-d]pyrimidinyl)acetic acid.

Also provided are aminoethylglycyl derivatives of the aforementioned acetic acid derivatives of pyrazolopyrimidine and pyrrolopyrimidine base analogues, wherein the α-amino group of a blocked glycyl moiety is derivatized to acetic acid C1 of the acetate and to C2 of an ethylamine moiety. These derivatives are also known as "PNA monomers." Such compounds are useful for automated synthesis of the aforementioned oligomers and polymers. Preferred embodiments of PPG-containing PNA monomers (also known as PPPG) include 5-[4-hydroxy-6-(2-methylpropanoylamino)pyrazolo[5,4-d]pyrimidinyl]-3-(2-{[(4-methoxyphenyl)diphenylmethyl]amino}ethyl)-4-oxopentanoic acid and 1-{6-[(1E)-aza-2-(dimethylamino)vinyl]-4-hydroxypyrzolo[5,4-d]pyrimidinyl}-N-(2-{[(4-methoxyphenyl)diphenylmethyl]amino}ethyl)-N-(2-oxypropyl)acetamide. A preferred embodiment of a PPA-containing PNA monomer is 2-[N-(2-{[(4-methoxyphenyl)diphenylmethyl]amino}ethyl)-2-{4-[(4-methoxyphenyl)carbonylamino]pyrazolo[5,4-d]pyrimidinyl}acetylamino] acetic acid.

Also provided are methods for the synthesis of oligomers comprising PNA, DNA, RNA and/or chimeras thereof, wherein the aforementioned PNA monomers are used at one or more steps in the synthesis. Oligomers synthesized by these methods are also provided.

In another embodiment, methods for detecting a target sequence in a polynucleotide by hybridization to a probe comprising a DNA, PNA, or PNA/DNA oligomer, wherein one or more residues in the probe comprises a pyrazolopyrimidine or pyrrolopyrimidine base analogue, are provided. In the practice of these methods, the probe can additionally comprise one or more of a ribonucleoside, a fluorophore, a fluorescence quencher and/or a minor groove binder.

In another embodiment, methods for detection of a target sequence in a polynucleotide utilizing compositions comprising a polymeric portion (comprising a polymer) and a fluorogenic portion (comprising one or more fluorophores), wherein one or more purine-containing residues of the polymer are substituted with a residue comprising a pyrazolopyrimidine and/or pyrrolopyrimidine base analogue, are provided. Polymers for use in the method can comprise PNA, DNA, RNA or chimeras thereof, and the base analogue can be present in any of the PNA, DNA or RNA portions of a chimeric polymer. Any number of purine residues in the polymer can be substituted by a base analogue. In a preferred embodiment, the method is practiced using a composition in which a purine residue in the polymeric portion that is directly adjacent to the fluorogenic portion is substituted with a pyrazolopyrimidine or a pyrrolopyrimidine. In another preferred embodiment, oligomers containing three or more consecutive G residues have their consecutive G residues replaced by PPG. Compositions for use in this method can optionally comprise a fluorescence quencher and/or a minor groove binder.

In additional embodiments, methods for detecting a target sequence in an amplification reaction, utilizing the compositions of the invention, are provided. In a preferred embodiment, the amplification reaction comprises a hydrolyzable probe assay.

Also provided are oligomer microarrays wherein at least one of the oligomers described herein is present on the array.

Methods for detecting a target sequence in a polynucleotide, wherein the polynucleotide is present in a sample, by hybridization to a composition as described herein are also provided. In a preferred embodiment, the target sequence has a single nucleotide mismatch with respect to a related sequence that is also present in the sample, and the composition forms a hybrid with the target sequence but not with the related sequence.

DETAILED DESCRIPTION

Figure 1:
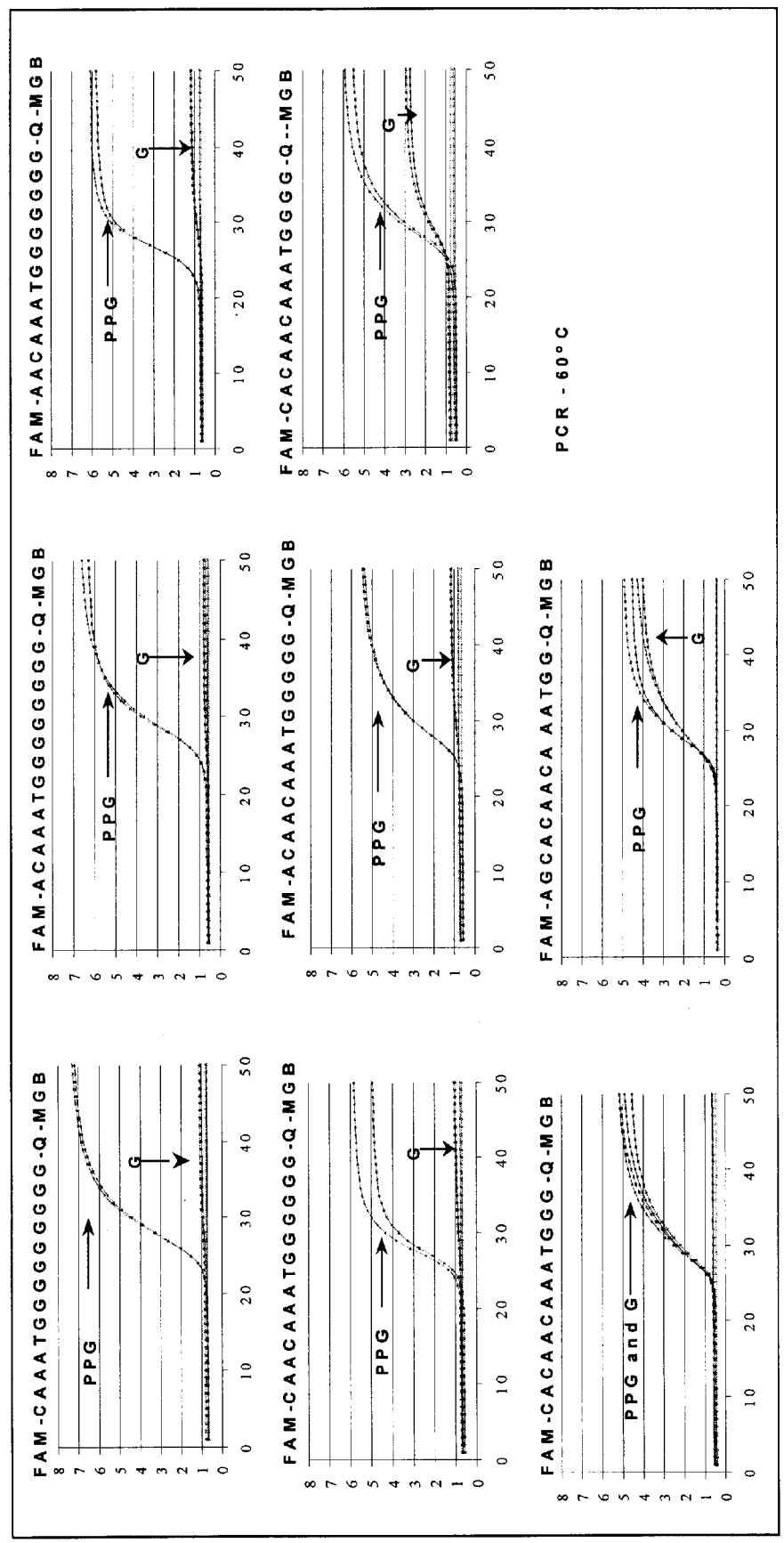
FIG. 1 shows real-time fluorescence analyses of a series of hydrolyzable probe assays in which probes containing G runs of between 2 and 9 nucleotides were used as fluorescent probes and compared to probes in which the G residues were substituted by PPG.

The practice of the invention will employ, unless otherwise indicated, conventional techniques in organic chemistry, biochemistry, oligonucleotide synthesis and modification, bioconjugate chemistry, nucleic acid hybridization, molecular biology, microbiology, genetics, recombinant DNA, and related fields as are within the skill of the art. These techniques are fully explained in the literature. See, for example, Maniatis, Fritsch & Sambrook, MOLECULAR CLONING: A LABORATORY MANUAL, Cold Spring Harbor Laboratory Press (1982); Sambrook, Fritsch & Maniatis, MOLECULAR CLONING: A LABORATORY MANUAL, Second Edition, Cold Spring Harbor Laboratory Press (1989); Ausubel, et al., CURRENT PROTOCOLS IN MOLECULAR BIOLOGY, John Wiley & Sons (1987 and annual updates); Gait (ed.), OLIGONUCLEOTIDE SYNTHESIS: A PRACTICAL APPROACH, IRL Press (1984); Eckstein (ed.), OLIGONUCLEOTIDES AND ANALOGUES: A PRACTICAL APPROACH, IRL Press (1991).

The disclosures of all publications and patents cited herein are hereby incorporated by reference in their entirety.

Definitions

The terms deazapurine and pyrrolopyrimidine are used interchangeably to indicate a heterocyclic nucleus comprising fused pyrimidine and pyrrole rings, according to the following general formula:

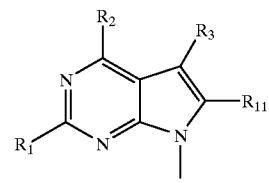

The term pyrazolopyrimidine refers to a heterocyclic nucleus comprising fused pyrimidine and pyrazole rings, according to the following general formula:

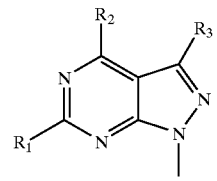

A "monomer" refers to a composition comprising a base or a base analogue covalently linked to a reactive moiety, such that the monomer can be incorporated, via the reactive moiety, as part of an oligomer or polymer. In certain cases, functional groups on the base/base analogue portion and/or on the reactive moiety are blocked so as not to be reactive during polymerization. In preferred embodiments, the reactive moiety is an aminoethylglycine moiety, in which case the monomer can be denoted a "PNA monomer."

An "oligomer" is a polymer comprising linked monomer units. Oligomers can be synthesized by sequential joining of monomers, via their reactive moieties, as is known in the art. An oligomer can comprise a DNA oligomer, a RNA oligomer, a PNA oligomer, or any chimeric oligomer made up of DNA, RNA, and/or PNA monomers.

A "blocking group" or "protecting group" is any chemical moiety capable of preventing reactivity of a N, S or O atom to which it is attached, under conditions in which such N, S or O atom might otherwise be reactive. Exemplary protecting groups include, but are not limited to tert-butyloxycarbonyl (tBoc), 4-methoxyphenyldiphenylmethyl (MMTr), isobutyryl (iBu), 9-fluoronylmethyloxycarbonyl (Fmoc), —C6H5 (benzyl), diphenylcarbamoyl (DPC), 2-N-dimethylvinyl (Dmv), benzyloxycarbonyl (Cbz), benzoyl (bz), isobutanoyl, acetyl, and anisoyl (An) groups. These and additional protecting groups useful in the synthesis of nucleic acid and PNA oligomers are known in the art. Uhlmann et al. (1998) Angew. Chem. Int. Ed. 37:2796–2823; Green, et al. in Protective Groups in Organic Synthesis, 2$^{nd}$ Edition, John Wiley and Sons, Inc, N.Y., pp. 441–452. 1991.

Oligomers

The invention provides oligomers in which one or more purine bases are substituted with a base analogue having the same base-pairing specificity as the purine which it replaces.

The analogues can be pyrazolopyrimidines or pyrrolopyrimidines. Oligomers can comprise DNA oligonucleotides, RNA oligonucleotides, PNA oligomers, or chimeras thereof. A chimera refers to an oligomer which comprises more than one type of subunit, e.g., a RNA/DNA chimera, a PNA/DNA chimera, a RNA/PNA chimera or a PNA/DNA/RNA chimera. For chimeric oligomers, a base analogue can be present in any portion of the chimera (i.e., in a DNA portion, a RNA portion and/or a PNA portion).

Methods for the synthesis of DNA, RNA and PNA oligomers are known in the art. See, for example, U.S. Pat. No. 5,419,966; Gait, supra; Eckstein (ed.) "Oligonucleotides and Analogues: A Practical Approach," 1991, IRL Press, Oxford; Ogilve et al. (1988) *Proc. Natl. Acad Sci. USA* 85:5746–5748; Nielsen et al. (1991) supra; Uhlmann et al. (1998) supra; U.S. Pat. Nos. 5,539,082; 5,714,331; 5,773, 571; 5,736,336 and 5,766,855. Additional modified DNA and/or RNA oligomers can also be used. For example, methods for the synthesis of 2'-O-methyl oligoribonucleotides have been described. Sproat et al. (1989) *Nucleic Acids Res.* 17:3373–3386.

In general, methods for oligomer synthesis comprise stepwise cycles of monomer addition to a growing oligomer chain that is optionally attached to a solid support, wherein the growing oligomer chain optionally contains protected functional groups and a blocked growing end. Typically, at each cycle of monomer addition, the support-bound growing chain is first subjected to conditions that de-block the growing end, then condensed with a monomer, which monomer is optionally activated for condensation. De-blocking conditions and reagents, as well as activating conditions and reagents, are known in the art. The monomer addition step is repeated as often as necessary, with the identity of the monomer added at each step corresponding with the desired sequence of the oligomer. When the desired sequence has been obtained, the nascent oligomer is subjected to conditions that deprotect functional groups and/or cleave the completed oligomer from the support, then purified, if necessary.

PNA oligomers are often used as substitutes for DNA oligonucleotides in various hybridization and other techniques. However, PNA oligomers are prone to aggregation and often exhibit reduced solubility in aqueous solvents, especially G-rich PNAs. In a preferred embodiment, a PNA oligomer comprises one or more residues in which a purine base is substituted by a pyrazolopyrimidine or pyrrolopyrimidine base analogue;- for example, G is substituted by PPG or 7-deazaguanine, A is substituted by PPA or 7-deazaadenine, and either G or A is substituted by PPI or 7-deazahypoxanthine. In this way the base analogue retains the base-pairing specificity of the base for which it is substituted. In a more preferred embodiment, a PNA oligomer with one or more G residues substituted by PPG is provided. Such PPG-substituted PNAs exhibit reduced intermolecular and intramolecular self-association compared to oligomers containing G. This facilitates purification and handling of the oligomers and provides improved hybridization properties (e.g., increased sensitivity), especially for probe sequences containing three or more consecutive G residues.

Because a base analogue retains the base-pairing specificity of the base it replaces, oligomers of the invention are capable of sequence-specific binding to complementary sequences and can exhibit enhanced duplex and triplex formation to single- and double-stranded targets, respectively.

Without wishing to be bound by any theory, applicants note that, when compared to naturally-occurring purine bases, pyrazolopyrimidine and pyrrolopyrimidine base analogues are less likely to form non-canonical base pairs (such and G-T and G-G base pairs), yet retain the ability to form canonical base pairs characteristic of the purines which they replace (i.e., PPG-C, 7PG-C, PPA-T and 7PA-T base pairs).

Base Analogues and their Synthesis

Base analogues in oligomers and in intermediates for oligomer synthesis are provided. The base analogues have a structure as indicated in Formula 1, wherein $R_1$ and $R_2$ are independently —H, —OH, —SH, or —$NH_2$; $R_3$ is —H, —CN, halogen (F, Cl, Br or I), or —$R_{12}$—Y, wherein $R_{12}$ is $C_1$–$C_{12}$ alkyl, alkenyl or alkynyl and Y is —H, —OH, —$NH_2$ or —SH; X is =CH— or =N—; and L is the linkage to an oligomer backbone, such as DNA, RNA, PNA or any chimera thereof.

Formula 1

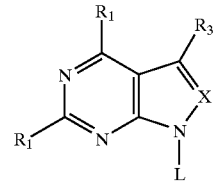

When X is =N—, the base analogues are pyrazolopyrimidines and when X is =CH—, the base analogues are pyrrolopyrimidines (also known as 7-deazapurines). For example, when X is =N—, $R_1$ is —OH, $R_2$ is —$NH_2$, and $R_3$ is —H, the base analogue is pyrazolopyrimidinylguanine (PPG). When X is =N—, $R_1$ is —$NH_2$, and $R_2$ and $R_3$ are —H, the base analogue is pyrazolopyrimidinyladenine (PPA). When X is =N—, $R_1$ is —OH, and $R_2$ and $R_3$ are —H, the base analogue is pyrazolopyrimidinylhypoxanthine (PPI).

When X is =C—, $R_1$ is —OH, $R_2$ is —$NH_2$, and $R_3$ is —H, the base analogue is 7-deazaguanine (7PG). When X is =C—, $R_1$ is —$NH_2$, and $R_2$ and $R_3$ are —H, the base analogue is 7-deazaadenine (7PA). When X is =C—, $R_1$ is —OH, and $R_2$ and $R_3$ are —H, the base analogue is 7-deazahypoxanthine (7PI).

PPG and 7-deazaguanine have the same base-pairing properties as guanine (i.e., base pair with C), while PPA and 7-deazaadenine have the same base-pairing properties as adenine (i.e., base pair with T and U). PPI and 7-deazahypoxanthine have base pairing properties equivalent to both G and A and therefore will pair with C, T and U.

Oligonucleotides comprising the base analogues are synthesized by automated methods that are well-known in the art, using precursors ("PNA monomers") according to Formula 3. The monomers are produced using intermediates having the structure represented in Formula 2.

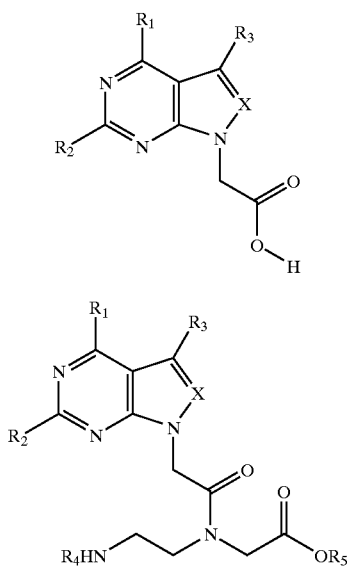

Formula 2

Formula 3

Allowed functional groups in Formulas 1 and 2 are as follows.

$R_1$ and $R_2$ are independently —H, —OH, —$OR_6$, —SH, —$NH_2$ or —$NHR_7$;

$R_3$ is —H, —CN, halogen (F, Cl, Br or I), or —$R_{12}$—Y, wherein $R_{12}$ is $C_1$–$C_{12}$ alkyl, alkenyl or alkynyl and Y is —H, —OH, —$NH_2$ or —SH;

$R_4$ is —H or a protecting group selected from the group consisting of tert-butyloxycarbonyl (tBoc), 4-methoxyphenyldiphenylmethyl (MMTr), isobutyryl (iBu) and 9-fluoronylmethyloxycarbonyl (Fmoc);

$R_5$ is —H or —$C_6F_4H$ (TFP);

$R_6$ is —H, —$C_6H_5$ (benzyl) or a diphenylcarbamoyl (DPC) group;

$R_7$ is a protecting group selected from the group consisting of 2-N-dimethylvinyl (Dmv), benzyloxycarbonyl (Cbz), monomethoxytrityl (MMtr), benzoyl (bz), isobutyryl (iBu), isobutanoyl, acetyl, and anisoyl (An) groups; and X is =CH— or =N—.

These formulas include all isomers and tautomers of the molecules signified thereby. Preferred embodiments of precursors for PNA synthesis and intermediates used in the synthesis of these precursors are as follows. When $R_1$ is —OH, $R_2$ is —$NH_2$, $R_3$ is —H and X is =N— in Formula 2, the resulting structure is 2-(6-amino-4-hydroxypyrazolo[5,4-d]pyrimidinyl)acetic acid (PPGA). When $R_1$ is —$NH_2$, $R_2$ is —H, $R_3$ is —H and X is =N— in Formula 2, the resulting structure is 2-(4-aminopyrazolo[5,4-d]pyrimidinyl)acetic acid (PPAA). The corresponding derivatives of Formula 3, wherein $R_4$ and $R_5$ are —H, are abbreviated MPPGA and MPPAA, respectively. Blocked derivatives of these compounds are also provided, as described infra.

The designation "pyrazolo[5,4-d]pyrimidine," as used herein, refers to the same structures that were designated pyrazolo[3,4-d]pyrimidines in previous co-owned publications, patents and patent applications. See, for example, U.S. Pat. No. 5,824,796; PCT WO 99/51621 and PCT WO 99/51775. The reason for this change in nomenclature is so that the names by which the structures are identified comply with those assigned to the structures by the nomenclature programs NamExpert and Nomenclator, provided by ChemInnovation Software, San Diego, Calif.

The synthesis of pyrazolopyrimidine and pyrrolopyrimidine bases is accomplished by methods known in the art. Seela et al. (1985) supra; Seela et al. (1986a), supra; Seela et al. (1986b), supra; and Seela et al. (1987) supra. Using the reactions described by Uhlmann et al. (1998) supra for the synthesis of 2-substituted purine acetic acid derivatives, appropriately protected 4-aminopyrazolo[5,4-d]pyrimidine (PPA) and 6-amino-4-hydroxypyrazolo[5,4-d]pyrimidine (PPG) can be reacted with alkyl 2-bromoacetate to give products of Formula 2. Since alkylation can occur on both the 1 and 2 nitrogen atoms of pyrazolopyrimidines, separation of isomers and purification of the 1-substituted isomer is required. In the case of 7-deazapurines and related pyrrolopyrimidines, reaction with alkyl 2-bromoacetate yields only the $N^1$-substituted product.

Accordingly, PPGA (3) can be synthesized from 4-methoxypyrazolo[5,4-d]pyrimidine-6-ylamine (4) (Seela et al. (1985) Heterocycles 23:2521–2524) by alkylation with ethyl 2-chloroacetate in the presence of sodium hydride, followed by separation of the isomers (Reaction Scheme 1).

Reaction Scheme 1

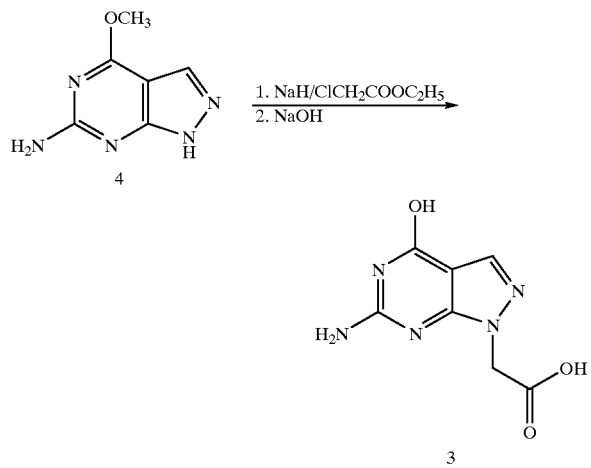

Another approach to the synthesis of PPGA is shown in Reaction Scheme 2. In this case, 2-amino-4-6-dichloropyrimidine-5-carboxyaldehyde (1) is reacted with ethyl 2-(hydrazinol)acetic acetate to give ethyl 2-(6-amino-4-{2-[(ethoxycarbonyl)methyl]hydrazino}pyrazolo[5,4-d]pyrimidinyl)acetate (2). Treatment of (2) with sodium hydroxide followed by hydrogen peroxide yields the desired product PPGA (3). An advantage of this synthetic procedure is that it yields only the $N^1$-substituted isomer. See Example 1, infra.

Reaction Scheme 2

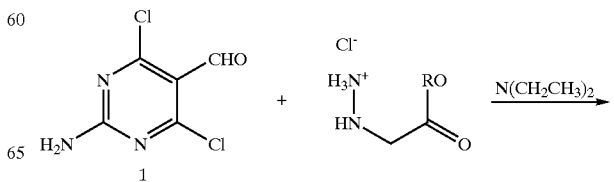

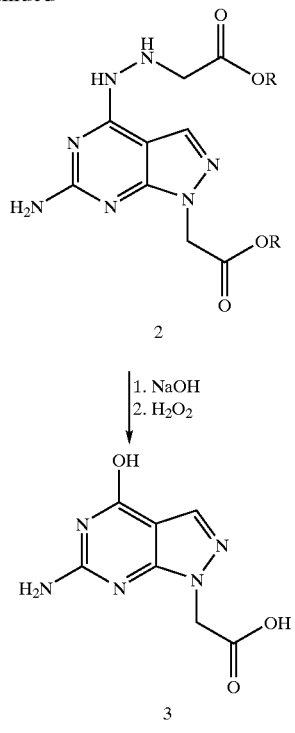

For use in automated chemical synthesis of oligomers, reactive groups on the base analogues, such as amino groups, must be protected. In one embodiment, blocked derivatives of PPGA are synthesized as described in Reaction Scheme 3. PPGA (3) is reacted with isobutanoyl chloride in dimethylformamide and triethylamine to generate a PPGA derivative with an isobutyryl-blocked amino group (14). See Example 2, infra.

Reaction Scheme 3

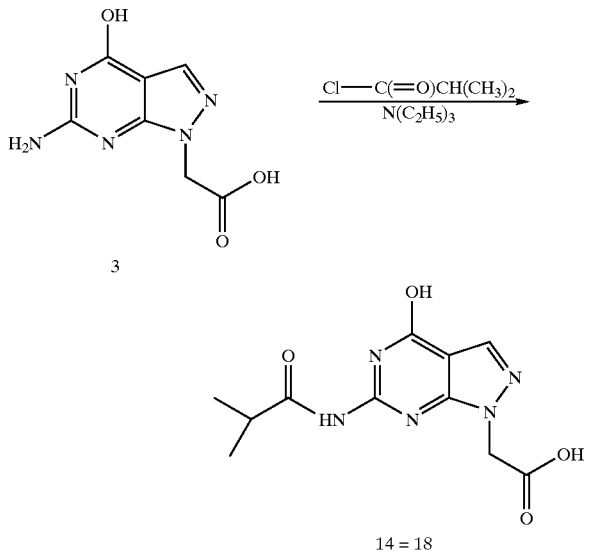

Methods for the synthesis of aminoethylglycyl derivatives of PPGA, PPAA, 2-(2-amino-4-hydroxypyrrolo[2,3-d]pyrimidin-7-yl)acetic acid (7PGA) and 2-(4-aminopyrrolo[2,3-d]pyrimidin-7-yl)acetic acid (7PAA), for use as monomers in automated oligomer synthesis, are known in the art.

Uhlmann et al, supra. These methods involve condensation of appropriately protected aminoethylglycine, e.g., methyl 2-[(2-{[(4-methoxyphenyl)diphenylmethyl]amino}ethyl)amino]acetate (MMTrAeg, Will et al. (1995) *Tetrahedron* 51:12069–12082) with any of PPGA, PPAA, 7PGA or 7PAA (also protected, if necessary) in the presence of a condensing reagent such as (O-7-azabenzotriazol-1-yl)-1,1,3,3-tetramethyluronium hexafluorophosphate (HATU), (benzotriazol-1-yl)-1,1,3,3-tetramethyluronium hexafluorophosphate (HBTU), or O-[(cyano(tethoxycarbonyl)methylen)amino]-1,1,3,3-tetramethyluronium tetrafluoroborate (TOTU), as shown in Reaction Scheme 4. The $R_5$ protecting group is chosen such that it can be removed selectively, (i.e., without removing other blocking groups) to yield a compound 7 in which $R_5$ is —H and, for example, $R_1$ is —NHCbz, $R_2$, and $R_3$ are —H and $R_4$ is —MMTr. This protected derivative of MPPAA is used in the synthesis of a PNA oligomer or a PNA/DNA chimera.

Reaction Scheme 4

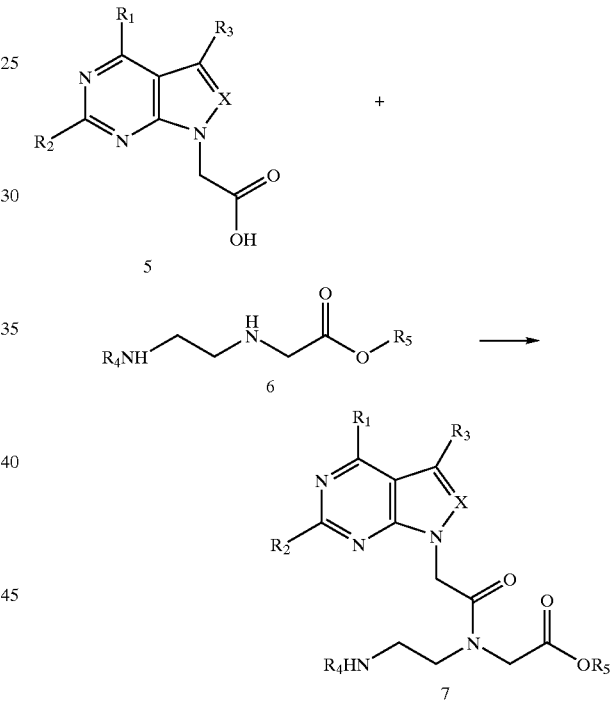

Exemplary synthesis of a blocked PPG monomer for PNA synthesis is accomplished according to Reaction Scheme 5. PPG (15) is reacted with isobutanoyl chloride to generate an amino-blocked PPG (16), which is treated with sodium hydride and then reacted with alkyl bromoacetate to generate, for example, a methyl acetate derivative (17). Alkaline hydrolysis of methyl ester 17 yields the acetic acid derivative 18. Further reaction of 18 with methyl 2-[(2-{[(4-methoxyphenyl)diphenylmethyl]amino}ethyl)amino]acetate (MMTrAeg) generates an alkyl ester (in this example, the methyl ester) of an MMTr-blocked aminoethylglycyl derivative with a MMTr-protected amino group (19), which, after alkaline hydrolysis of the ester, yields the MMTr-protected aminoethylglycine derivative 20. See Example 3, infra.

Reaction Scheme 5

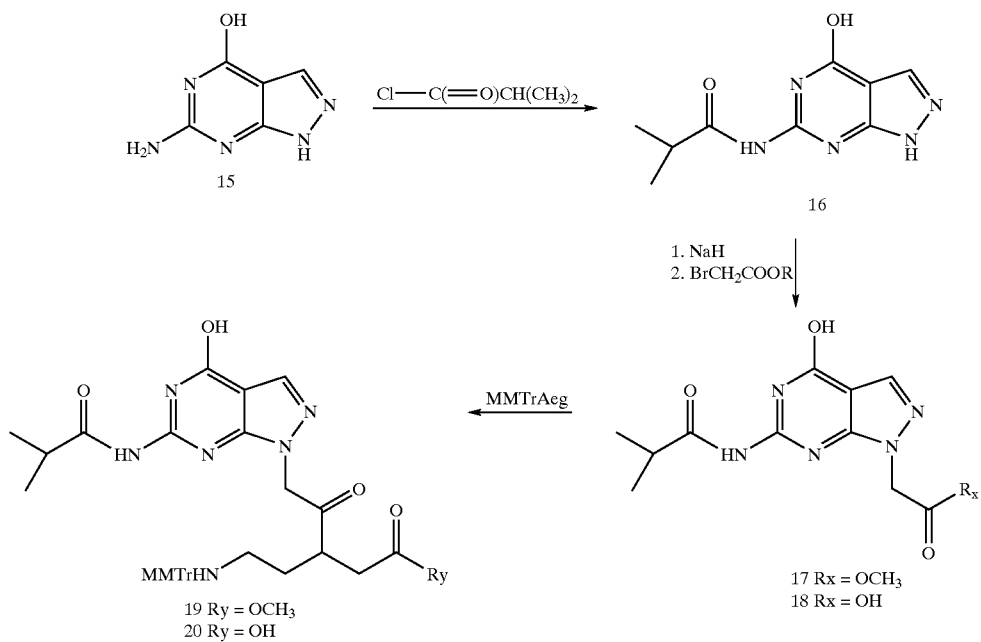

An exemplary method for synthesis of a PNA monomer comprising the base analogue PPA is shown in Reaction Scheme 6. 4-aminopyrazolo[5,4-d]pyrimidine (PPA, Compound 8) is reacted with 4-methoxybenzoyl chloride in pyridine to yield the amino-protected PPA derivative (9). This is reacted with sodium hydride followed by the 2-bromoacetate methyl ester, and the $N^1$-substituted methylacetate derivative (10) is isolated. Treatment of 10 with sodium hydroxide converts the methyl ester to the N-Bz-protected acetate derivative of PPAA (Compound 11). See Example 4 for details.

Reaction Scheme 6

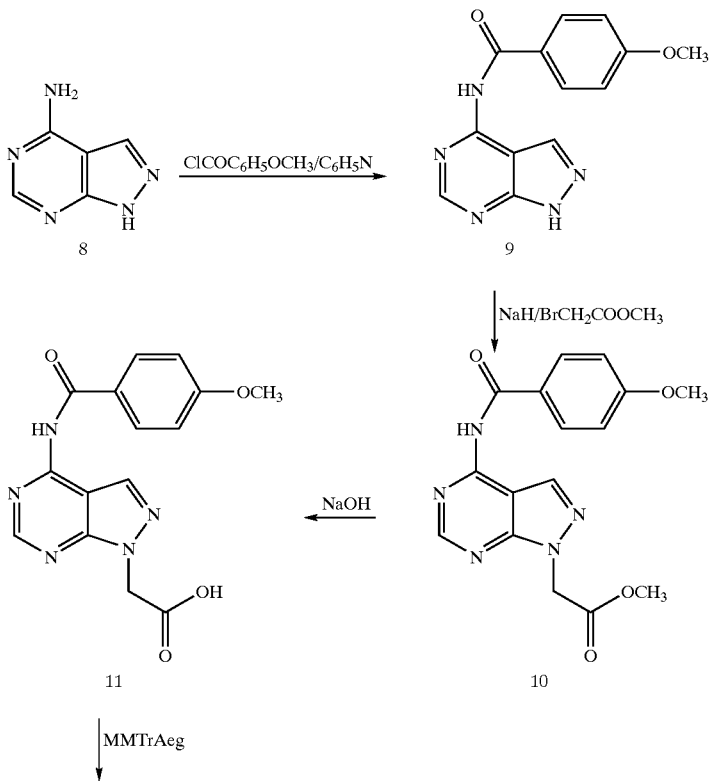

-continued

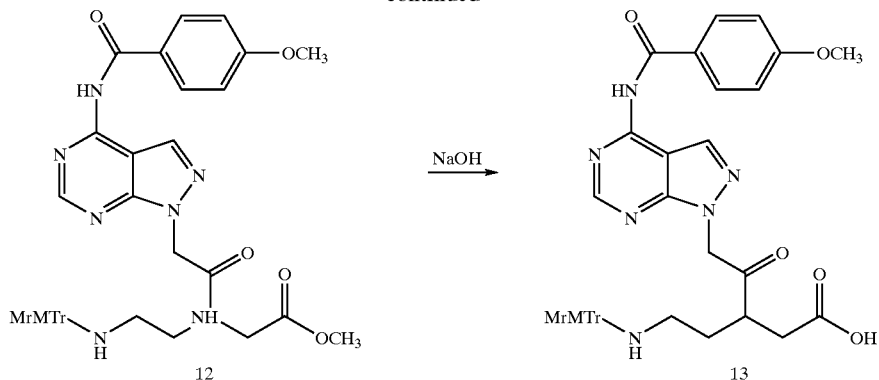

Continuing with Reaction Scheme 6, conversion of N-Bz PPAA (11) to a reactive monomer for PNA synthesis proceeds by condensation of 11 with monomethoxytritylaminoethylaminoacetate (MMTrAeg = monomethoxytritylaminoethylglycine) to form 12, followed by treatment of 12 with alkali to generate the MMTr-protected aminoethylglycine derivative 13. See Example 5 for details.

A preferred PPG monomer is the 2-N-dimethylvinyl protected MMTr-aminoethylgycine derivative (24), whose synthesis is shown in Reaction Scheme 7. 4-methoxypyrazolo[5,4]pyrimidine-6-ylamine (21) was reacted first with KOH in dry methanol, followed by reaction with methyl bromoacetate to give the methyl acetate derivative (22). Alkaline hydrolysis to yield the acetic acid derivative 23 was followed by reaction with (dimethoxymethyl)dimethylamine to give (24). Reaction of (24) with MMTrAeg yielded the protected PPG monomer 25.

Reaction Scheme 7

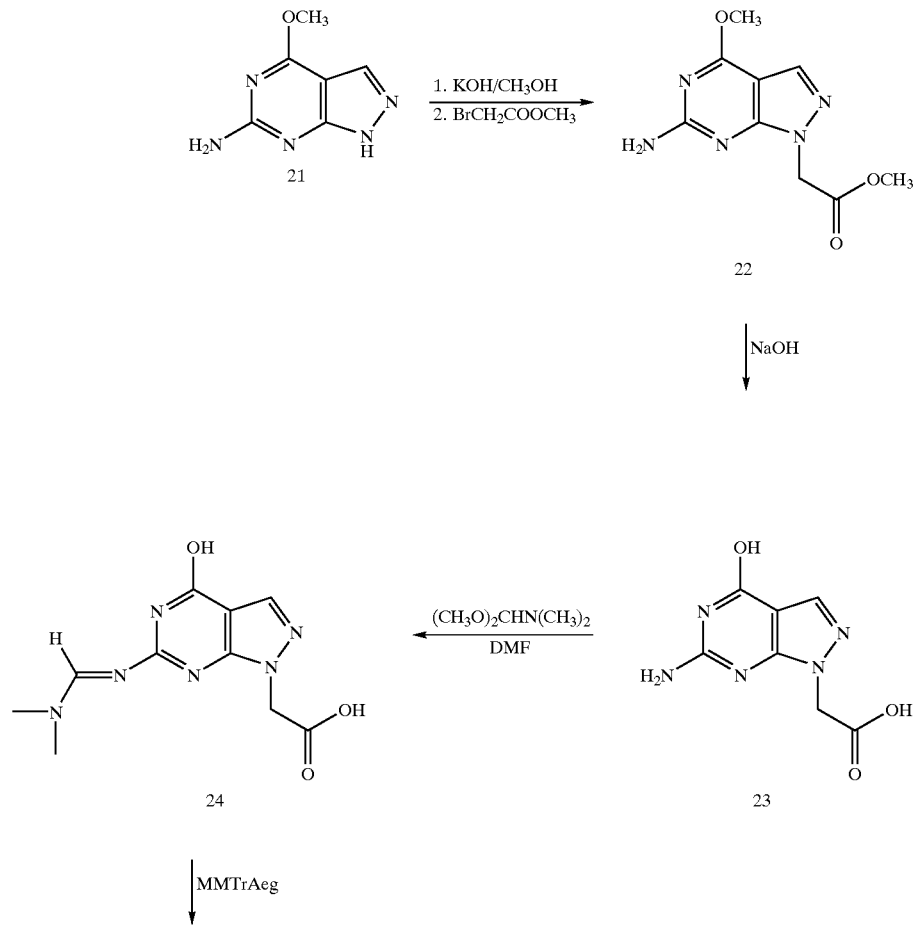

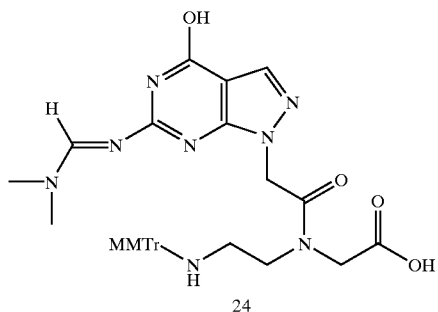

24

A preferred PPA monomer is the 2-N-dimethylvinyl protected MMTr-aminoethylglycine derivative (29), whose synthesis is shown in Reaction Scheme 8. Pyrazolo[5,4]pyrimidin-4-ylamine (8) was reacted first with KOH in dry methanol followed by reaction with methyl bromoacetate to give the methyl acetate derivative (26). This was reacted with (dimethoxymethyl)dimethylamine to give (27), which was treated with NaOH to yield (28). Reaction of (28) with MMTrAeg yielded the PPA monomer (29).

Reaction Scheme 8

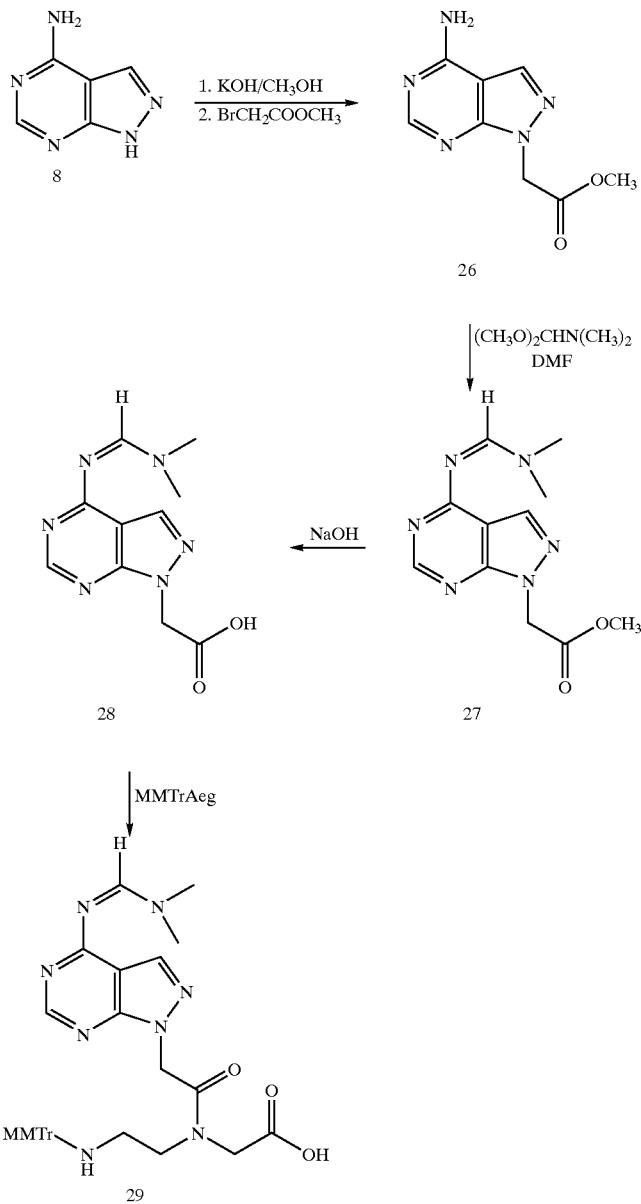

Synthesis of reactive derivatives of PPI follows similar procedures. Pyrazolo[5,4-d]pyrimidin-4-ol (PPI, Tominaga et al. (1990) *J. Heterocycl. Chem.* 27:775–783) can be alkylated directly with methyl bromoacetate, followed by alkaline hydrolysis, to yield 2-(4-hydroxypyrazolo[5,4-d] pyrimidinyl)acetic acid, which can be converted as described (Uhlmann et al. (1998) supra) to the MMTr-blocked aminoethylglycine derivative. Alternatively, the hydroxyl group of PPI could be blocked with a diphenyl-carbamoyl group before reaction with methyl bromoacetic acetate.

The same synthetic approaches used to synthesize reactive derivatives of pyrazolo[5,4-d]pyrimidines can be used to synthesize reactive derivatives of 7-deazapurines for use in the synthesis of PNA-containing oligomers. The basic difference between the synthesis of these two types of compounds is that in the latter case only one isomer is generated following alkylation with methyl bromoacetate.

Synthesis of PNA-containing Oligomers

In addition to the monomers and precursors described supra, the invention includes PNA oligomers, DNA oligonucleotides and/or PNA/DNA chimeras comprising at least one monomeric unit of Formula 4, optionally covalently attached to one or more ligands, tail moieties or pendant groups. A PNA oligomer comprises two or more PNA monomers that are covalently linked by peptide bonds, as illustrated in Formula 4, where B is a base (i.e. a heterocyclic base A, G, C, T or U as are commonly found in nucleic acids or a modified derivative thereof) or base analogue; k is between 0 and 50, preferably between 0 and 40, more preferably between 0 and 30, and still more preferably between 0 and 20; and $R_{21}$ are independently —H, —OH, —NH$_2$, —NHR$_{22}$, —N(R$_{22}$)$_2$, a protecting group, a reactive group or an oligomer, where $R_{22}$ is —H or $C_{1-6}$ alkyl, alkenyl or alkynyl.

Formula 4

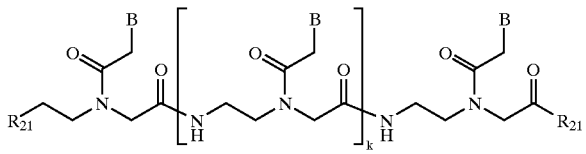

The synthesis of PNA oligomers from monomeric precursors is known in the art. See, for example, Uhlmann et al., supra. Synthesis is begun with a CPG resin or other solid support, containing a conjugated amino group. An appropriately blocked monomer (corresponding to the terminal monomer of the desired oligomer) is covalently coupled to the amino group with the aid of a coupling reagent. After deprotection of the blocked growing end of the first monomer, a second monomer is coupled. The process is repeated until an oligomer of the desired length and sequence is obtained, at which time the oligomer is cleaved from the solid support and any base protecting groups are removed.

In one embodiment, a PNA oligomer contains a —NH$_2$ group at the end that was cleaved from the solid support, and a —COOH or —OH group at the opposite end. The terminal functional groups provide sites for the attachment of additional molecules and pendant groups to the PNA-containing oligomer.

Strategies for the synthesis of PNA/DNA chimeric oligomers are well known in the art. See, for example, Uhlmann et al., supra. Two principal strategies for the synthesis of PNA/DNA chimeras are block condensation of presynthesized PNA and DNA oligomers in solution and stepwise solid phase synthesis with suitably protected PNA and DNA monomeric precursors. Those skilled in the art will appreciate that, depending on the method of synthesis, different connecting groups between the PNA and DNA portions are possible. Exemplary linkages include, but are not limited to, N-(2-hydroxyethyl)glycine and 5'-amino-2',5'-dideoxynucleoside phosphoramidite linkages. Uhlmann et al., supra.

Coupling reagents (or activating agents) for use in the condensation of PNA monomers to form a PNA oligomer include, but are not limited to, benzotriazolyl-1-oxy-trispyrrodinophosphonium hexafluorophosphate (PyBOP), O-(7-azabenzotriazol- 1-yl)-1,1,3,3-tetramethyluronium hexafluorophosphate (HATU), O-(7-benzotriazol- 1-yl)-1,1, 3,3-tetramethyluronium hexafluorophosphate (HBTU), dicyclohexylcarbodiimide (DCC)/1-hydroxybenzotriazole (HOBt), N,N'-diisopropylcarbodiimide (DIC), bromo tris (pyrrolidino)phosphonium hexafluorophosphate (ByBrop), and O-[(cyano(ethoxycarbonyl)methylene)amino}1,1,3,3-tetramethyluronium tetrafluorborate (TOTU). These and additional activating and condensing agents are known to those of skill in the art. See, for example, Uhlmann et al., supra.

Additional molecules which can be covalently coupled to an oligomer include, but are not limited to, intercalators, lipophilic groups, minor groove binders, major groove binders, reporter groups (including fluorescent, chemiluminescent and radioactive reporters), proteins, enzymes, antibodies, chelating agents and/or cross-linking agents. These molecules can be attached internally and/or at one or both ends of the oligomer. The nature and attachment of such molecules to oligonucleotides are presently well known in the art, and are described, for example, in U.S. Pat. Nos. 5,512,667 and 5,419,966 and in PCT publication WO 96/32496, which are incorporated herein by reference.

The oligomers of the invention can also have a relatively low molecular weight tail moiety attached at either or both ends. By way of example, a tail molecule can be a phosphate, a phosphate ester, an alkyl group, an aminoalkyl group, a hydrophilic group or a lipophilic group. The tail moiety can also link an intercalator, lipophilic group, minor groove binder, reporter group, chelating agent and/or cross-linking functionality to the oligomers of the invention. The nature of tail moieties and methods for obtaining oligonucleotides with various tail moieties are also described in the above-referenced U.S. Pat. Nos. 5,512,667 and 5,419,966.

Molecules can be attached to an oligomer of the invention to modify its solubility in aqueous solvents. Such molecules include, but are not limited to, saccharides and charged molecules such as amino acids, charged minor groove binders, and the like.

In a preferred embodiment, oligomers of the invention containing PPG substituted for guanine and/or PPA substituted for adenine also comprise a conjugated minor groove binder (MGB). Optimal single-nucleotide mismatch discrimination is obtained using MGB-conjugated oligonucleotides containing PPG in place of guanine, as disclosed in co-owned PCT publication WO 99/51775. Polar MGBs are preferred; more preferred MGB moieties include the trimer of 3-carbamoyl-1,2-dihydro-(3H)-pyrrolo[3,2-e]indole-7-carboxylate (CDPI$_3$) and the pentamer of N-methylpyrrole-4-carbox-2-amide (MPC$_5$). Additional MGB moieties that will find use in the practice of the present invention are disclosed in co-owned U.S. Pat. No. 5,801,155 and co-owned PCT publication WO 99/51621, the disclosures of which are incorporated herein by reference.

Oligomers can comprise base analogues in addition to the purine analogues disclosed herein such as, for example, modified pyrimidines and pyrimidine analogues.

Furthermore, the oligomers of the invention can comprise backbones other than a peptide backbone, or can comprise heterogeneous backbones made up of mixed peptide and non-peptide linkages. For example, oligomers with backbones based on glycine methyl esters, ornithine, proline, diaminocyclohexane and the phosphoramidite of 2-aminopropanediol can be used. Uhlmann et al., supra. In addition, PNAs in which the peptide bond is replaced by a phosphonic acid bridge, such as N-(2-aminoethyl) phosphonoglycine and N-(2-hydroxyethyl) phosphonoglycine, can be used. Peyman et al. (1997) *Angew. Chem. Intl. Ed. Engl.* 36:2809–2812; Efimov et al. (1998) *Nucl. Acids. Res.* 26:566–577. Additional oligomer linkages will be apparent to those of skill in the art.

Triplex-forming Oligomers

PNA-containing oligomers are useful for detection of both single-stranded and double-stranded nucleic acid targets. For detection of double-stranded nucleic acids, an oligomer binds in the major groove of a double-stranded target via Hoogsteen, reverse Hoogsteen or equivalent base pairing, as is known in the art. See, for example, Fresco, U.S. Pat. No. 5,422,251; Hogan, U.S. Pat. No. 5,176,996; and Lampe (1997) *Nucleic Acids Res.* 25:4123–4131. Substitution of purines by base analogues in a PNA-containing oligomer, as disclosed herein, facilitates triplex formation. Triplex-forming oligonucleotides optionally contain conjugated groups, such as fluorophores, fluorescent quenchers and any of the additional molecules described supra. In a preferred embodiment, a triplex-forming PNA-containing oligomer with one or more purines substituted by a base analogue comprises a conjugated minor groove binder. See supra for disclosure of minor groove binders useful in the oligomers of the invention.

Fluorophores and Fluorescence Quenchers

In one embodiment, an attached reporter group is a fluorescent label or a fluorophore/fluorescent quencher pair. In a preferred embodiment, the replacement of one or more purine residues by pyrazolopyrimidine and/or pyrrolopyrimidine base analogues, in a probe containing a fluorescent label, results in reduced quenching of the label. Accordingly, fluorescently-labeled probes comprising one or more purine analogues, optionally comprising a fluorescence quencher, are provided.

Fluorescent labels include, but are not limited to, dyes such as fluoresceins, rhodamines, naphthylamines, coumarins, xanthenes, acridines, benzoxadiazoles, stilbenes, pyrenes, cyanines, phycoerythrins, green fluorescent proteins, and the like. Additional fluorescent labels, and methods for their conjugation to nucleic acid and PNA probes, are known to those of skill in the art. See, for example, Haugland (1996) *Handbook of Fluorescent Probes and Research Chemicals,* Sixth edition, Molecular Probes, Inc., Eugene, Oreg. and PCT publication WO 99/40226. In general, methods for attachment of a fluorescent label and/or a fluorescence quencher to a PNA oligomer or a PNA portion of a chimeric oligomer are similar to those used for conjugating a fluorophore and/or fluorescence quencher to a DNA oligonucleotide. The fluorophore or quencher is either attached to a tail moiety comprising a reactive group such as, for example, —OH or —NH$_2$; or is attached to a base, for example, at the position of a pyrimidine, the 7-position of a purine, or the 3-position of a pyrazolopyrimidine or pyrrolopyrimidine.

In certain embodiments of the present invention, oligomers comprising both a fluorescent label (fluorophore) and a fluorescence quencher are used. A fluorescence quencher is also referred to as a quenching portion of a probe or polymer. Fluorescence quenchers include those molecules whose absorption spectrum overlaps the fluorescence emission spectrum of a particular fluorophore, such that they are capable of absorbing energy emitted by a fluorophore so as to reduce the amount of fluorescence emitted (i.e., quench the emission of the fluorescent label). Different fluorophores are quenched by different quenching agents. In general, the spectral properties of a particular fluorophore/quencher pair are such that one or more absorption wavelengths of the quencher overlaps one or more of the emission wavelengths of the fluorophore.

Appropriate fluorophore/quencher pairs, in which emission by the fluorophore is absorbed by the quencher, are known in the art. See, for example, Haugland, supra. Exemplary pairs of fluorescence quencher/fluorophore pairs which can be used in the practice of the invention are as follows. A preferred fluorophore/quencher pair is fluorescein and tetramethylrhodamine. Nitrothiazole blue quenches fluorescence emission of six different dyes, namely 6-FAM, dR110, dR6G, dTMR, dROX and JAZ. Lee et al. (1999) *Biotechniques* 27:342–349. 6-carboxytetramethylrhodamine (TAMRA) quenches emission from 6-carboxyfluorescein (FAM) and 6-carboxy-4,7,2',7'-fluorescein (TET). Lee et al. (1993) *Nucl. Acid Res.* 21:3671–3766. 6-(N-[7-nitrobenz-2-oxa-1,3-diazol-4-yl]amino) hexanoic acid quenches fluorescence by 7-dimethylaminocoumarin-4-acetate. Bicket et al. (1994) *Ann. NY Acad. Sci.* (September 6)732:351–355. 6-carboxy-X-rhodamine (ROX) and erythromycin B quench FAM emission. Li et al. (1999) *Bioconj. Chem.* 10:241–245. The 2,4-dinitrophenyl group quenches (R,S)-2-amino-3-(7-methoxy-4-coumaryl)propanoic acid. Hawthorne et al. (1997) *Anal. Chem.* 253:13–17. Dabcyl is used as a quencher of dansyl sulfonamide in chemosensors and in fluorogenic peptides as a quencher for the fluorophore EDANS. Rothman et al. (1999) *Bioorg. Med. Chem. Lett.* 22:509–512 and Matayoshi et al. (1990) *Science* 247:954–958. QSY-7 is a quencher of tetramethylrhodamine. Haugland supra. Additional fluorophore/quencher pairs can be selected by those of skill in the art by comparison of emission and absorption wavelengths according to the properties set forth above.

Although any fluorescent label is useful in the practice of the invention, preferred fluorophores have emission maxima between 400 and 800 nm. Similarly, although any fluorescence quencher is useful, preferred fluorescence quenchers have absorption maxima between 400 and 800 nm.

In a further embodiment, an oligomer comprises a pair of fluorophores capable of fluorescence resonance energy transfer (FRET). In this case, two fluorophores are used in a FRET series. The first fluorophore (fluorescence donor) has an emission spectrum that overlaps the excitation spectrum of the second fluorophore (fluorescence acceptor). Accordingly, irradiation at the excitation wavelengths of the fluorescence donor results in fluorescence at the emission wavelength of the acceptor. It is clear that any number of fluorophores, having appropriate overlap of their emission and excitation wavelengths, can form a FRET series or three, four or more fluorophores.

In one embodiment, a fluorophore is a latent fluorophore, as disclosed in co-owned U.S. patent application Ser. No.09/428,236, entitled "Hybridization triggered fluorescent detection of nucleic acids" filed Oct. 26, 1999.

Exemplary Advantages

When an oligomer is used as a probe or primer, substitution of base analogues for purines reduces aggregation of the substituted oligomer, both with itself and with other oligomer molecules. Reduction of aggregation was demonstrated for G-rich probes as described in Example 6, infra. Consequently, improved methods for detection of target sequences by hybridization, using oligomers as probes, are obtained using the oligomers disclosed herein. Target sequences can comprise DNA, RNA, or any oligo- or polynucleotide.

Replacement of purines by base analogues in fluorescently-labeled probes reduces quenching of the label that occurs in unsubstituted probes. See Examples 7 and 8, infra. In particular, the inventors have determined that detection of amplification product using probes containing more that three consecutive G residues adjacent to a fluorescent label is inefficient and, for probes containing 5 or more consecutive G residues adjacent to a fluorescent label, no detection of product is observed. The inventors have also determined that, when PPG is substituted for G, fluorescent probes containing up to 9 consecutive PPG residues adjacent to a fluorescent label provide highly efficient detection of amplification products. Accordingly, improved methods for detecting a target sequence which utilize probes comprising a polymeric portion (typically an oligomer, preferably a PNA oligomer or a PNA/DNA chimera, more preferably a DNA oligomer) and a fluorescent portion are obtained using the compositions disclosed herein.

Thus, DNA, RNA, PNA and chimeric oligomers, comprising pyrazolopyrimidine and pyrrolopyrimidine base analogues as disclosed herein, are useful in techniques including, but not limited to, hybridization, primer extension, hydrolyzable probe assays, amplification methods (e.g., PCR, SSSR, NASBA), single nucleotide mismatch discrimination, allele-specific oligonucleotide hybridization, nucleotide sequence analysis, hybridization to oligonucleotide arrays, in situ hybridization and related techniques. Oligomers disclosed herein can be used as immobilized oligomers in oligomer arrays such as those described in, for example, U.S. Pat. Nos. 5,492,806; 5,525,464; 5,556,752 and PCT publications WO 92/10588 and WO 96/17957. Improved specificity and sensitivity likely result from increased solubility, decreased tendency for aggregation, reduced quenching of conjugated fluorogenic labels, and/or some combination of these and other factors.

Improved performance of PPG-substituted probes in a real-time hydrolyzable probe assay is demonstrated in Example 9, infra.

In another embodiment of the invention, a PNA-containing oligomer with one or more purine residues substituted by a base analogue is used as a pharmaceutical, for example as an antisense or anti-gene reagent, as a component of a ribozyme, or for gene therapy. Therapeutic uses include D-loop formation in vivo or ex vivo.

The following examples are provided to illustrate, but not to limit, the invention.

EXAMPLES

Example 1

Synthesis of 2-(6-amino-4-hydroxypyrazolol[5,4-d]pyrimidinyl)acetic acid (PPGA, Compound 3)

Ethyl-2-(6-amino-4-{2-[ethoxycarbonyl)methyl]hydrazino}pyrazolo[5,4-d]pyrimidinyl)acetate (Compound 2)

2-Amino-4-6-dichloropyrimidine-5-carboxyaldehyde (Compound 1) (10 g; 52 mmole) is treated with a solution of 10.1 g (64.8 mmole) of ethyl 2-(hydrazinol)acetic acetate hydrochloride in 100 ml water. Triethylamine (15 ml; 107 mmole) was added and the mixture was heated to 60° C. for 10 min, then stirred at room temperature for 3 days. Although ethyl 2-(hydrazinol)acetic acetate hydrochloride did not dissolve completely, TLC on $SiO_2$ ($CH_2Cl_2$:$CH_3OH$ 10:1) showed the formation of new product. The mixture was evaporated to dryness, taken up in toluene (100 ml) and evaporated to dryness. The solid was suspended in about 300 ml $CH_3CN$ and filtered through a $SiO_2$ column (49×6 cm), washed with 0.71 of $CH_3CN$ and about 300 ml of $CHCl_3$.

The filtrate was evaporated to dryness, dissolved in 120 ml hot $CH_3OH$ and crystallized overnight at 4° C. The product, a colorless solid (3.2 g) was collected and dried. TLC and reversed phased HPLC indicated a pure compound and NMR analysis supported structure 2.

2-(6-amino-4-hydroxypyrazolo[5,4-d]pyrimidinyl) acetic acid (Compound 2)

Compound 2 (3.16 g; 9.4 mmole) was dissolved in 100 ml of hot methanol, then 100 ml of a 2N NaOH solution was added, and the mixture was refluxed for 6 hours, at which time analysis by TLC indicated hydrolysis of the ester. Product 3 (PPGA) was formed by the addition of 2 ml of 30% $H_2O_2$ (in portions of 0.5 ml) to the reaction mixture, followed by heating to 80° C., until generation of $O_2$ from degradation of excess $H_2O_2$ was complete. Methanol was removed by heating at 100–120° C., followed by cooling to room temperature and addition of 17 ml of concentrated HCl to give a pH of about 4. Precipitation of the product initiated at this point, and was facilitated by the addition of ice. The product was filtered, washed with cold water and dried over NaOH and $P_2O_5$ (yield 3.9 g). NMR confirmed the structure and indicated the presence of about 4–8 molecules of $H_2O$ per molecule of product.

Example 2

Synthesis of 2-[4-hydroxy-6-(2-methylpropanoylamino)pyrazolo[5,4-d]pyrimidinyl] acetic acid (14)

PPGA (Compound 3, 5.58 g; 20 mmole) is suspended in anhydrous DMF (40 ml) and triethylamine (4.29 ml; 30.8 mmole). Isobutanoyl chloride (2.12 g; 19.9 mmole) is added dropwise using a syringe. The mixture is stirred at 100° C. for 3 hours, then treated with methanol and evaporated to dryness. The residue is treated with 20 ml 1N HCl and then with methanol and evaporated to dryness. The residue is treated with hot isopropanol and the precipitated product is filtered off and dried in vacuo. The product (14) is analyzed by TLC and HPLC and, if necessary, is purified further by chromatography.

Example 3

5-[4-hydroxy-6-(2-methylpropanoylamino)pyrazolo [5,4-d]pyrimidinyl]-3-(2-{[(4-methoxyphenyl) diphenylmethyl]amino}ethyl)-4-oxopentanoic acid (20)

N-(4-hydroxypyrazolo[5,4-d]pyrimidin-6-yl)-2-methylpropanamide (16)

Compound 15 (PPG, 3.02 g; 20 mmole) is suspended in anhydrous DMF (40 ml) and triethylamine (1.45 ml, 10.4 mmole), and isobutanoyl chloride (2.12 g, 19.9 mmole) is added dropwise using a syringe. The mixture is stirred at 100° C. for 3 hours. The reaction mixture is then treated with methanol and evaporated to dryness. The residue is treated with methanol and evaporated to dryness. The residue is then treated with hot isopropanol and the precipitated product (16) is filtered off and dried in vacuo. The product is analyzed by TLC and HPLC and, if necessary, is further purified by chromatography.

Methyl 2-[4-hydroxy-6-(2-methylpropanoylamino) pyrazolo[5,4-d]pyrimidinyl]acetate (17)

Compound 16 (4.42 g; 20 mmole) is suspended in dry DMF (40 ml), sodium hydride (0.5 g; 20.8 mmole) is added in portions, and the mixture is stirred at room temperature for 60 min. Methyl bromoacetate (1.9 ml; 20.6 mmole) is then added at room temperature, by syringe, and stirring is continued at room temperature. At completion of the reaction (monitored by TLC), the reaction mixture is treated with a small amount of carbon dioxide in methanol. The solvent is then evaporated and the residue dissolved in $CH_2Cl_2$, washed once with water and then evaporated to dryness. The product is purified by chromatography to yield the desired isomer (17).

2-[4-Hydroxy-6-(2-methylpropanoylamino)pyrazolo [5,4-d]pyrimidinyl]acetic acid (18)

Compound 17 (4.41 g; 15 mmole) is suspended in 25 ml water, and a 2N aqueous solution of sodium hydroxide is added drop-wise at 0° C., while maintaining the pH at 11, until the methyl ester is completely hydrolyzed. The reaction solution is then filtered, and the filtrate is brought to pH 3 using 2 M $KHSO_4$ solution, then extracted with ethyl acetate. The aqueous phase is evaporated and the product (18) is purified by chromatography.

Methyl 5-[4-hydroxy-6-(2-methylpropanoylamino) pyrazolo[5,4-d]pyrimidinyl]-3-(2-{[(4-methoxyphenyl)diphenylmethyl]amino}ethyl)-4-oxopentanoate (19)

Methyl 2-[(2-{[(4-methoxyphenyl)diphenylmethyl] amino}ethyl)amino]acetate (MMTrAeg, 1.26 g; 3.1 mmole) is dissolved in DMF (8 ml). To this solution is added N-ethylmorpholine (1.07 g; 6.28 mmole), 3-hydroxy-4-oxo-3,4-dihyro-1,2,3-benzotrazine (HOObt) (0.505 g; 3.1 mmole), Compound 18 (0.91 g; 3.1 mmole) and diisopropylcarbodiimide (DIPC) (0.59 g; 3.72 mmole). The reaction mixture is stirred for 48 hours at 4° C., at which time the solvent is evaporated and the residue dissolved in ethyl acetate. The ethyl acetate solution is washed with water and washed once with saturated KCl solution. The organic phase is then dried over $Na_2SO_4$, filtered and evaporated. The residue is dissolved in a small volume of ethyl acetate and cooled on ice to induce crystallization of diisopropylurea, leaving the product 19 in the aqueous phase. Alternatively, the diisopropylurea is separated by silica gel chromatography from compound 19.

5-[4hydroxy-6-(2-methylpropanoylamino)pyrazolo [5,4-d]pyrimidinyl]-3-(2-{[(4-methoxyphenyl) diphenylmethlyl]amino}ethyl)4-oxopentanoic acid (20)

Compound 19 (1.33 g; 2 mmole) is dissolved in 10 ml dioxane. This solution is cooled to 0° C. and 1 M aqueous NaOH (8.66 ml) is added drop-wise in 5 aliquots over 2.5 hours. After an additional 2 hours at room temperature the solution is adjusted to pH 5 by drop-wise addition of 2 M $KHSO_4$. Precipitated salts are filtered off and washed with dioxane, and the combined filtrates are evaporated. The residue is co-evaporated with ethanol and methanol/$CH_2Cl_2$, then purified by silica gel chromatography to yield (20).

Example 4

Synthesis of 2-{4-[4-Methoxyphenyl) carbonylamino]pyrazolo[5,4-d]pyrimidinyl}acetic acid (Compound 11, Reaction Scheme 6)

4-(Methoxyphenyl)-N-pyrazolo[4,5-d]pyrimidin-4-ylcarboxamide (9)

Pyrazolo[5,4-d]pyrimidine-4-ylamine (8) (13.5 g; 0.10 mole) is suspended in dry pyridine (250 ml), and 4-methoxybenzolyl chloride (17.1 g; 0.1 mole) is added drop-wise using a syringe. The mixture is heated at 100° C. until TLC shows that the reaction is complete (about 1 to 3 hours). The cooled reaction is then treated with methanol and the solvent evaporated. The residue is co-evaporated twice with toluene and then stirred with hot isopropanol. This mixture is cooled slowly and the precipitated product (9) is filtered off and evaluated for purity by TLC and HPLC. If necessary, the product is further purified by chromatography.

Methyl 2-{4-[(4-methoxyphenyl)carbonylamino] pyrazolo[5,4-d]pyrimidinyl}acetate (10)

Compound (9) (6.7 g; 25 mmole) is suspended in 75 ml of dry DMF. Sodium hydride (0.65 g; 27 mmole) is added in portions, and the mixture is stirred at room temperature for 30 min. Methyl bromoacetate (2.44 ml; 26.5 mmole) is added at room temperature using a syringe. Stirring is continued at room temperature until analysis by TLC indicates completion of the reaction, at which time the reaction mixture is treated with a small amount of carbon dioxide in methanol. The solvent is evaporated and the residue is dissolved in $CH_2Cl_2$, washed once with water and then evaporated to dryness. The product is purified by chromatography to yield the desired isomer (10).

2-{4-[4-Methoxyphenyl)carbonylamino]pyrazolo[5, 4-d]pyrimidinyl}acetic acid (11)

Compound (10) (5.13 g; 15 mmole) is suspended in 120 ml water, and 2N aqueous sodium hydroxide solution is added drop-wise at 0° C. to maintain the pH at 11, until the methyl ester is completely hydrolyzed. The reaction solution is filtered and the pH of the filtrate is brought to 3, using 2 M $KHSO_4$ solution, leading to the precipitation of product (11). The precipitate is washed with a small amount of water, dried in vacuo, and analyzed for purity. If necessary, the product (11) is purified further by chromatography.

Example 5

Synthesis of 2-[N-(2-{[(4-methoxyphenyl) diphenylmethyl]amino}ethyl)-2-{4-[(4-methoxyphenyl)carbonylamino]pyrazolo[5,4-d] pyrimidinyl}acetylamino]acetic acid (Compound 13, Reaction Scheme 6)

Methyl 2-[N-(2-{[(4-methoxyphenyl) diphenylmethyl]amino}ethyl)-2-{4-[(4-methoxyphenyl)carbonylamino]pyrazolo[5,4-d] pyrimidinyl}acetylamino]acelate (12)

Methyl 2-[(2-{[(4-methoxyphenyl)diphenylmethyl] amino}ethyl)amino]acetate (MMTrAeg, 1.26 g; 3.1 mmole) is dissolved in DMF (8 ml). To this solution is added N-ethylmorpholine (1.07 g; 6.28 mmole), 3-hydroxy-4-oxo-3,4-dihyro-1,2,3-benzotrazine (HOObt) (0.505 g; 3.1 mmole), Compound 11(1.01 g; 3.1 mmole) and diisopropylcarbodiimide (DIPC) (0.59 g; 3.72 mmole). The reaction mixture is stirred for 48 hours at 4° C., then the solvent is removed in vacuo and the residue is dissolved in ethyl acetate. This solution is washed with water and washed once with saturated KCl solution. The organic phase is dried over $Na_2SO_4$, filtered and evaporated. The residue is dissolved in a small volume of ethyl acetate and cooled in ice to induce crystallization of diisopropylurea, leaving the product (12) in solution. Alternatively, diisopropylurea is separated from (12) by silica gel chromatography.

2-[N-(2-{[(4-Methoxyphenyl)diphenylmethyl] amino}ethyl)-2-{4-[(4-methoxyphenyl) carbonylamino]pyrazolo[5,4-d] pyrimidinyl}acetylamino]acetic acid (13)

Compound (12) (1.43 g; 2 mmole) is dissolved in dioxane (10 ml). The solution is cooled to 0° C., and 1 M aqueous NaOH (8.66 ml) is added drop-wise in 5 aliquots over 2.5 hours. After an additional 2 hours at room temperature, the pH is adjusted to 5 by drop-wise addition of 2 M $HKSO_4$. Precipitated salts are filtered off, washed with dioxane, then the combined filtrates are dried in vacuo. The residue (13) is co-evaporated with ethanol and methanol/$CH_2Cl_2$, then purified by silica gel chromatography.

Example 6

Reduction in Self-association of PPG-containing Oligonucleotides

In this example, 13-mer and 14-mer oligonucleotide conjugates, containing between two and nine G residues, were analyzed by nondenaturing gel electrophoresis and compared with oligonucleotides of identical sequence except that all G residues were replaced by PPG. The lengths and sequences of the oligonucleotides are given in Table 1. Electrophoresis was conducted in 8% polyacrylamide gels run in 1×TBE buffer for 45 min at 40° C. Gels were stained with Daiichi 2D Silver Stain II® and $R_f$ values for the stained oligonucleotide bands were determined using two control oligonucleotides as standards. Control oligonucleotide A had the sequence 5'-ACCTGTATTCCTTGCC-3' (SEQ ID NO. 22) and control oligonucleotide B had the sequence 5'-ZTACAZCAAATZZAA-3' (SEQ ID NO. 23), where Z represents PPG.

TABLE 1

Oligonucleotide Sequences

| Sequence* | Length | SEQ ID NO. (with G) | SEQ ID NO. (with PPG) |
|---|---|---|---|
| 5'-CAAATGGGGGGGGG-3' | 14 | 1 | 9 |
| 5'-ACAAATGGGGGGGG-3' | 14 | 2 | 10 |
| 5'-AACAAATGGGGGGG-3' | 14 | 3 | 11 |
| 5'-CAACAAATGGGGGG-3' | 14 | 4 | 12 |
| 5'-ACAACAAATGGGGG-3' | 14 | 5 | 13 |
| 5'-CACAACAAATGGGG-3' | 14 | 6 | 14 |
| 5'-CACAACAAATGGG-3' | 13 | 7 | 15 |
| 5'-AGCACAACAAATGG-3' | 14 | 8 | 16 |

*All oligonucleotides contained, at their 5' ends, a conjugated fluorescein moiety and, conjugated at their 3' ends, a minor groove binder ($CDPI_3$) and a quencher (tetramethylrhodamine). Synthesis of this type of conjugate is described in co-owned PCT Publication WO 99/51775, the disclosure of which is incorporated by reference.

Results of the analysis are shown in Table 2. $R_f$ values were measured separately for G- and PPG-containing oligonucleotides with respect to control oligonucleotides A and B, respectively. However, the distance migrated by control oligonucleotide A and B was essentially identical. Oligonucleotides containing three or more G residues (oligonucleotides 1–6) show a reduction in Rf when compared to similar-sized oligonucleotides containing two G residues or less (e.g., oligonucleotides 7 and 8 and control oligonucleotide A), indicating aggregation of G-rich oligonucleotides. By contrast, oligonucleotides containing between two and nine PPG residues have $R_f$'s that are similar to one another and to a control oligonucleotide containing two PPG residues. It was also noted that G-containing oligonucleotides exhibited diffuse bands upon electrophoresis (the $R_f$ values for these oligonucleotides was determined by measuring from the center of the band). Furthermore, comparison of a G-containing oligonucleotide with an oligonucleotide of the same size and sequence, but with G substituted by PPG, shows that the reduced $R_f$ characteristic of oligonucleotides containing three or more G residues is not observed with PPG-containing oligonucleotides, suggesting little or no aggregation of oligonucleotides containing up to nine consecutive PPG residues.

TABLE 2

Rf values of G- and PPG-containing oligonucleotides

| SEQ ID NO | # G | # PPG | $R_f$ |
|---|---|---|---|
| A | 2 | | 1.00 |
| 1 | 9 | | 0.58 |
| 2 | 8 | | 0.42 |
| 3 | 7 | | 0.37 |
| 4 | 6 | | 0.35 |
| 5 | 5 | | 0.32 |
| 6 | 4 | | 0.29 |
| 7 | 3 | | 0.96 |
| 8 | 2 | | 0.96 |
| B | | 4 | 1.00 |
| 9 | | 9 | 0.96 |
| 10 | | 8 | 0.97 |
| 11 | | 7 | 0.95 |
| 12 | | 6 | 0.95 |
| 13 | | 5 | 0.98 |
| 14 | | 4 | 1.03 |
| 15 | | 3 | 0.98 |
| 16 | | 2 | 0.96 |

Example 7

Reduced Fluorescence Quenching in Fluorescently-labeled Nucleotides when PPG is Substituted for G Fluorescein was coupled to GMP and to PPGMP (i.e., the monophosphate derivatives of G and PPG) and the fluorescence of 200 nM solutions of these conjugates was determined. Excitation was at 494 nm and fluorescence emission was measured at 522 nm. Fluorescence emission of the GMP conjugate was 15,447 units; while the fluorescence emission of the PPGMP conjugate was 32,767 units. Thus, quenching of the fluorophore by guanine was relieved when PPG was substituted for guanine, leading to an increase in fluorescence yield of the PPGMP conjugate of over two-fold, compared to the G conjugate.

Example 8

Reduced Fluorescence Quenching in Fluorescently-labeled Oligonucleotide Probes when PPG is Substituted for G Fluorescein-oligonucleotide conjugates were examined for the effect, on fluorescence yield, of substituting PPG for G. The oligonucleotide portion of the conjugates contained a 5'-terminal G or PPG residue, to which was coupled a fluorescein molecule. The conjugates optionally contained a covalently coupled $CDPI_3$ molecule at their 3'-end. Sequences are given in Table 3. Fluorescence of a 200 nM solution of the conjugates, in 20 mM Tris-HCl, pH 7, 40 mM NaCl, 5 mM $MgCl_2$, was measured at room temperature, with excitation at 494 nm and emission detected at 522 nm. Results are given in Table 3.

TABLE 3

Effect of PPG substitution on fluorescence yield of oligonucleotide conjugates

| SEQ ID No | Sequence* | F† | ΔF‡ | % increase |
|---|---|---|---|---|
| 18 | 5'-Fl-GTCCTGATTTTAC-MGB-3' | 8,650 | | |
| 19 | 5'-Fl-(PPG)TCCTGATTTTAC-MGB-3' | 10,739 | 2,089 | 24 |
| 20 | 5'-Fl-GTCCTGATTTTAC-3' | 14,883 | | |
| 21 | 5'-Fl-(PPG)TCCTGATTTTAC-3' | 23,835 | 8,952 | 38 |

*- Fl denotes fluorescein; MGB denotes a conjugated minor groove binder ($CDPI_3$)
†- denotes fluorescence yield, in arbitrary units
‡- indicates the increase in fluorescence of a PPG-containing oligonucleotide, compared to a G-containing oligonucleotide The results indicated that substitution of PPG for G increased fluorescence (i.e., reduced quenching) by 24% and 38% for MGB-conjugated and non-MGB-conjugated oligonucleotides, respectively.

Example 9

Improved Performance of Probes Containing Multiple Consecutive G Residues in a Hydrolyzable Probe Assay when PPG is Substituted for G The oligonucleotide conjugates whose sequences are shown in Table 1 were used as fluorescent probes in a hydrolyzable probe assay. U.S. Pat. No. 5,210,015; Livak et al. (1995) *PCR Meth. App.* 4:357–362; Wittwer et al. (1997a) *Biotechniques* 22:130–138; and Wittwer et al. (1997b) *Biotechniques* 22:176–181. The performance of G-containing probes was compared to that of PPG-containing probes. Probes contained a conjugated fluorophore at their 5' end, along with a quencher and a minor groove binder conjugated to the 3' end of the probe, as described in co-owned PCT publication WO 99/51775. The target sequence was 5'-CACCTCAGCCTCCCAAGTAA-CTTTTAACCCCCCCCCATTTGTTGTGCTGTTTTCAT-ACCTGTAATCCTGGCACTTT-3' (SEQ ID NO. 17). Underlined portions of the target sequence correspond to the primer sequences.

Amplification was conducted in an Idaho Technologies LC-24 LightCycler® with real-time fluorescence monitoring. Amplification reactions contained $10^5$ copies/µl of the target 76-mer (as above), 100 nM of each primer, 10 nM fluorescent probe (as above), 20 mM Tris-HCl, pH 7, 40 mM NaCl, 5 mM $MgCl_2$, 0.05% bovine serum albumin, 0.5 mM each dNTP, 0.038 Unit/µl Taq polymerase and 0.01 Unit/µl Uracil-N-glycosylase. The cycling program was one cycle of 50° C. for 3 min, then 95° C. for 2 min, followed by 50 cycles of 95° C. for 2 sec, then 60° C. for 30 sec.

The results are shown in FIG. 1. In this method, production of amplification product is indicated by an increase in fluorescence with time, caused by hydrolysis of the probe hybridized to the amplification product. The results obtained herein show that detection of amplification product using probes containing more that three consecutive G residues was inefficient and, in fact, for probes containing 5 or more consecutive G residues, no detection of product was observed. By contrast, when PPG was substituted for G in the fluorescent probe, probes containing up to 9 consecutive PPG residues provided highly efficient real-time detection of amplification product.

Although the foregoing invention has been described in some detail by way of illustration and example for purposes of clarity of understanding, it will be apparent to those skilled in the art that various changes and modifications can be practiced without departing from the spirit of the invention. Therefore the foregoing descriptions and examples should not be construed as limiting the scope of the invention.

What is claimed is:

1. An oligomer comprising one or more peptide nucleic acid (PNA) residues, wherein one or more of said PNA residues comprises a base having the formula

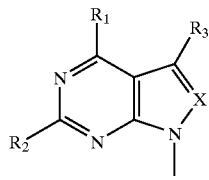

wherein $R_1$ and $R_2$ are independently —H, —OH, —$OR_6$, —SH, $NH_2$, or —$NHR_7$;

$R_3$ is —H, —CN, halogen (F, Cl, Br or I), or —$R_{12}$—Y, wherein $R_{12}$ is $C_1$–$C_{12}$ alkyl, alkenyl or alkynyl and Y is —H, —OH, —$NH_2$ or —SH;

$R_6$ is —$C_6H_5$ (phenyl) or a diphenylcarbamoyl (DPC) group;

$R_7$ is a protecting group selected from the group consisting of dimethylamino(methylene), benzyloxycarbonyl (Cbz), monomethoxytrityl (MMtr), benzoyl (bz), isobutyryl (iBu), isobutanoyl, acetyl and anisoyl (An) groups; and X is =CH— or =N—;

provided that when $R_1$ is —$NH_2$ and $R_2$ is H, then X is N.

2. An oligomer according to claim 1, wherein the oligomer comprises one or more DNA nucleotides.

3. An oligomer according to claim 1, wherein the oligomer is a peptide nucleic acid.

4. An oligomer according to claim 1, wherein the oligomer is a PNA/DNA chimera.

5. An oligomer according to claim 1, further comprising a minor groove binder.

6. An oligomer according to claim 1, further comprising a fluorophore.

7. An oligomer according to claim 6, further comprising a fluorescence quencher.

8. An oligomer according to claim 7, further comprising a minor groove binder.

9. An oligomer according to claim 4, further comprising a fluorophore.

10. An oligomer according to claim 9, further comprising a fluorescence quencher.

11. An oligomer according to claim 10, further comprising a minor groove binder.

12. An oligomer according to claim 4, further comprising a minor groove binder.

13. An oligomer according to claim 12, further comprising a fluorophore.

14. A conjugate comprising:

(a) a polymer comprising a plurality of monomer units; and (b) a fluorophore covalently attached thereto;

wherein one or more of the monomer units comprises a base analogue, wherein each of the base analogues is independently selected from the group consisting of pyrazolopyrimidines and pyrrolopyrimidines having the structure

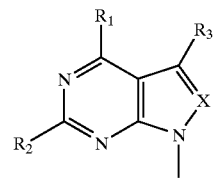

wherein $R_1$ and $R_2$ are independently —H, —OH, —SH, or —$NH_2$;

$R_3$ is —H, —CN, halogen (F, Cl, Br or I), or —$R_{12}$—Y, wherein $R_{12}$ is $C_1$–$C_{12}$ alkyl, alkenyl or alkynyl and Y is —H, —OH, —$NH_2$ or —SH; and X is =CH— or =N—; provided that when $R_1$ is —$NH_2$ and $R_2$ is H, then X is =N—, such that the base analogues retain the base-pairing specificity of the bases for which they are substituted and lead to reduced quenching of the fluorophore, reduced self-association of the polymer or both reduced quenching of the fluorophore and reduced self-association of the polymer.

15. The conjugate of claim 14, having at least four consecutive purine residues in the polymer, wherein at least one of the at least four consecutive purine residues in the polymer is substituted by a base analogue.

16. The conjugate of claim 15, further comprising a fluorescence quencher.

17. The conjugate of claim 15 wherein the polymer comprises DNA.

18. The conjugate of claim 15 wherein the polymer comprises peptide nucleic acid (PNA).

19. The conjugate of claim 15 wherein the polymer comprises a PNA/DNA chimera.

20. The conjugate of claim 19, wherein the base analogue is present in the DNA portion of the polymer.

21. The conjugate of claim 19, wherein the base analogue is present in the PNA portion of the polymer.

22. The conjugate of claim 14, wherein X is =N—.

23. The conjugate of claim 22, wherein the base analogue is selected from the group consisting of pyrazolopyrimidinyladenine (PPA), pyrazolopyrimidinylguanine (PPG) and pyrazolopyrimidinylhypoxanthine (PPI).

24. The conjugate of claim 14, wherein X is =CH—.

25. The conjugate of claim 24, wherein the base analogue is selected from the group consisting of 7-deazaadenine, 7-deazahypoxanthine and 7-deazaguanine.

26. The conjugate of claim 16, wherein the fluorophore emits between 400 and 800 nm.

27. The conjugate of claim 26, wherein the quencher absorbs between 400 and 800 nm.

28. The conjugate of claim 15, further comprising a minor groove binder.

29. An oligomer microarray, comprising one or more oligomers according to claim 1.

30. An oligomer microarray comprising one or more oligomers according to claim 15.

31. The conjugate of claim 15, wherein the base analogue is selected from the group consisting of pyrazolopyrimidinyladenine (PPA), pyrazolopyrimidinylguanine (PPG) and pyrazolopyrimidinylhypoxanthine (PPI).

32. The conjugate of claim 31, wherein the base analogue is pyrazolopyrimidinylguanine (PPG).

33. The conjugate of claim 15, wherein the purine residue is guanine.

34. The conjugate of claim 33, wherein the base analogue is selected from the group consisting of pyrazolopyrimidinyladenine (PPA), pyrazolopyrimidinylguanine (PPG) and pyrazolopyrimidinylhypoxanthine (PPI).

35. The conjugate of claim 34, wherein the base analogue is pyrazolopyrimidinylguanine (PPG).

36. An oligomer according to claim 1, wherein $R_3$ is —CN, halogen (F, Cl, Br or I), or —$R_{12}$—Y, wherein $R_{12}$ is $C_1$–$C_{12}$ alkyl, alkenyl or alkynyl and Y is —H, —OH, —$NH_2$ or —SH.

37. An oligomer according to claim 36, wherein the oligomer comprises one or more DNA nucleotides.

38. An oligomer according to claim 36, wherein the oligomer is a peptide nucleic acid.

39. An oligomer according to claim 36, wherein the oligomer is a PNA/DNA chimera.

40. An oligomer according to claim 39, further comprising a fluorophore.

41. An oligomer according to claim 40, further comprising a fluorescence quencher.

42. An oligomer according to claim 41, further comprising a minor groove binder.

43. An oligomer according to claim 39, further comprising a minor groove binder.

44. An oligomer according to claim 43, further comprising a fluorophore.

45. An oligomer according to claim 36, further comprising a minor groove binder.

46. An oligomer according to claim 36, further comprising a fluorophore.

47. An oligomer according to claim 46, further comprising a fluorescence quencher.

48. An oligomer according to claim 47, further comprising a minor groove binder.

49. An oligomer microarray, comprising one or more oligomers according to claim 36.

50. The conjugate of claim 15, wherein three or fewer consecutive purine residues remain in the polymer once the substitution has been made.

51. The conjugate of claim 50, wherein the purine residue is guanine.

52. The conjugate of claim 15, wherein two or fewer consecutive purine residues remain in the polymer once the substitution has been made.

53. The conjugate of claim 52, wherein the purine residue is guanine.

54. The conjugate of claim 33 having from 2–9 consecutive guanine residues, wherein the 2–9 guanine residues are substituted by an equal number of pyrazolopyrimidinylguanines (PPGs).

55. A conjugate according to claim 14, wherein $R_3$ is —CN, halogen (F, Cl, Br or I), or —$R_{12}$—Y, wherein $R_{12}$ is $C_1$–$C_{12}$ alkyl, alkenyl or alkynyl and Y is —H, —OH, —$NH_2$ or —SH; and X is =CH—.

* * * * *